US010016376B2

(12) United States Patent
Cho et al.

(10) Patent No.: US 10,016,376 B2
(45) Date of Patent: Jul. 10, 2018

(54) COMPOSITION FOR ALLEVIATING NEPHROTOXICITY CAUSED BY IMMUNOSUPPRESSIVE DRUG, COMPRISING METFORMIN, AND COMPOSITION FOR PREVENTING OR TREATING IMMUNE DISEASE, COMPRISING THE SAME

(71) Applicant: THE CATHOLIC UNIVERSITY OF KOREA INDUSTRY-ACADEMIC COOPERATION FOUNDATION, Seoul (KR)

(72) Inventors: Mi La Cho, Seoul (KR); Chul Woo Yang, Seoul (KR); Jong Young Choi, Seoul (KR); Sung Hwan Park, Seoul (KR); Min Jung Park, Seoul (KR); Seon Yeong Lee, Seoul (KR); Joo Yeon Jhun, Seoul (KR); Eun Jung Lee, Namyangju-si (KR); Jae Kyung Kim, Cheonan-si (KR); Eun Kyung Kim, Seoul (KR); Sun Woo Lim, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/537,486

(22) PCT Filed: Dec. 18, 2015

(86) PCT No.: PCT/KR2015/013977
§ 371 (c)(1),
(2) Date: Jun. 19, 2017

(87) PCT Pub. No.: WO2016/099214
PCT Pub. Date: Jun. 23, 2016

(65) Prior Publication Data
US 2017/0348256 A1 Dec. 7, 2017

(30) Foreign Application Priority Data

Dec. 18, 2014 (KR) .................. 10-2014-0183462
Dec. 15, 2015 (KR) .................. 10-2015-0179374

(51) Int. Cl.
A61K 31/155 (2006.01)
A61K 38/13 (2006.01)
A61K 31/436 (2006.01)

(52) U.S. Cl.
CPC .......... A61K 31/155 (2013.01); A61K 31/436 (2013.01); A61K 38/13 (2013.01)

(58) Field of Classification Search
CPC ..... A61K 31/155; A61K 31/436; A61K 38/13
USPC ....................................................... 514/20.5
See application file for complete search history.

(56) References Cited

FOREIGN PATENT DOCUMENTS

| KR | 10-2001-0030749 A | 4/2001 |
| KR | 10-2003-0007104 A | 1/2003 |
| KR | 10-0443730 B1 | 10/2004 |
| KR | 10-2010-0063827 A | 6/2010 |
| KR | 10-2013-0129496 A | 11/2013 |
| KR | 10-2014-0132932 A | 11/2014 |

OTHER PUBLICATIONS

Noack et al., "Th17 and regulatory T cell balance in autoimmune and inflammatory diseases", Autoimmunity Reviews, vol. 13, pp. 668-677, (2014).
Miossec et al., "Targeting IL-17 and TH17 cells in chronic inflammation", Nature Reviews, vol. 11, pp. 763-776, (2012).
Dalal et al., "Role of tacrolimus combination therapy with mycophenolate mofetil in the prevention of organ rejection in kidney transplant patients", International Journal of Nephrology and Renovascular Disease, vol. 3, pp. 107-115, (2010).
Janjua et al., "Protective effect of metformin against gentamicin induced nephrotoxicity in rabbits", Pak. J. Pharm. Sci., vol. 27, No. 6, pp. 1863-1872, (2014).
Wood et al., "Regulatory immune cells in transplantation", Nature Reviews, vol. 12, pp. 417-430, (2012).
Liu et al., "T cell-directed therapies: lessons learned and future prospects", Nature Immunology, vol. 8, No. 1, pp. 25-30, (2007).
Ji et al., "Negative Regulation of Intracellular Cytokine Signal Transduction" The Journal of the Korean Rheumatism Association, vol. 10, No. 1, pp. 1-8, (2003).
Morales et al., "Metformin prevents experimental gentamicin-induced nephropathy by a mitochondria-dependent pathway", Kidney International, vol. 77, pp. 861-869, (2010).
Shivaswamy et al., "Metformin Improves Immunosuppressant Induced Hyperglycemia and Exocrine Apoptosis in Rats", Transplantation, vol. 95, pp. 280-284, (2013).
Son et al., "Metformin Attenuates Experimental Autoimmune Arthritis through Reciprocal Regulation of Th17/Treg Balance and Osteoclastogenesis", Mediators of Inflammation, vol. 2014, Article ID 973986, 13 pages, (2014).

(Continued)

Primary Examiner — Kristin A Vajda
(74) Attorney, Agent, or Firm — Vorys, Sater, Seymour and Pease LLP; Mih Suhn Koh

(57) ABSTRACT

Provided is a composition for alleviating nephrotoxicity caused by an immunosuppressive drug, including metformin, and a composition for preventing or treating an immune disease, including the same. Further, the composition provided can be useful in improving a treatment effect on diseases requiring immunosuppression by effectively alleviating a decline in renal function caused due to side effects of conventional immunosuppressive drugs, and can also be useful in preventing or treating organ transplant rejection, autoimmune diseases, inflammatory diseases and the like since various methods of co-administering a conventional immunosuppressive drug and metformin are suggested to reduce nephrotoxic side effects of conventional immunosuppressive drugs and maximize immunosuppressive or immunomodulatory effects.

11 Claims, 17 Drawing Sheets

(56) References Cited

OTHER PUBLICATIONS

Rafieian-Kopaei et al., "Efficacy of Co-administration of Garlic Extract and Metformin for Prevention of Gentamicin-Renal Toxicity in Wistar Rats: A Biochemical Study", Int J Prev Med, vol. 4, pp. 258-264, (2013).

Naesens et al., "Calcineurin Inhibitor Nephrotoxicity", Clin J Am Soc Nephrol, vol. 4, pp. 481-508, (2009).

Kim et al., "Application of Regulatory T Cells in Transplantation Field", J Korean Soc Transplant, vol. 26, pp. 74-82, (2012).

COMPOSITION FOR ALLEVIATING NEPHROTOXICITY CAUSED BY IMMUNOSUPPRESSIVE DRUG, COMPRISING METFORMIN, AND COMPOSITION FOR PREVENTING OR TREATING IMMUNE DISEASE, COMPRISING THE SAME

CROSS-REFERENCE TO RELATED APPLICATION

This application claims priority to and the benefit of Korean Patent Application No. 10-2014-0183462, filed on Dec. 18, 2014, and Korean Patent Application No. 10-2015-0179374, filed on Dec. 15, 2015, the disclosures of which are incorporated herein by reference in its entirety.

BACKGROUND

1. Field of the Invention

The present invention relates to a composition for alleviating nephrotoxicity caused by an immunosuppressive drug, including metformin, and a composition for preventing or treating an immune disease, including the same, and more particularly, to a composition for reducing nephrotoxicity caused by an immunosuppressive drug, including metformin as an active ingredient, a pharmaceutical composition for preventing or treating an immune disease, including metformin and an immunosuppressive drug such as a calcineurin inhibitor as active ingredients, and a pharmaceutically combined preparation for preventing or treating an immune disease, including metformin and an immunosuppressive drug such as a calcineurin inhibitor as constituent elements, wherein the metformin and the calcineurin inhibitor are administered simultaneously, separately, or in a predetermined order.

2. Discussion of Related Art

Immunosuppressive drugs are drugs that block or reduce a humoral immune response in which antibodies are generated against antigens or cellular immune response, and thus have been generally used to treat immune rejection caused after organ transplantation, or graft-versus-host diseases after bone marrow transplantation.

In addition, the immunosuppressive drugs are of importance for use to treat autoimmune diseases such as lupus, rheumatoid arthritis, and the like, hypersensitive immune responses such as allergy, atopy, and the like, and inflammatory diseases over a long period of time.

Immunosuppressive drugs currently used in the art are divided into corticosteroids, antimetabolites, calcineurin inhibitors, mammalian targets of rapamycin inhibitors, antibodies, and the like, depending on their mechanisms of action. These drugs have an immunosuppressive effect by blocking the proliferation or activation of T cells in the immune system at different stages (Dalal, P. et al. Int. J. Nephrol. Renovasc. Dis. 3:107-115 (2010)). T cells which are a main target of the immunosuppressive drugs differentiate into two categories: type 1 T helper cells (Th1) which are generated in the human thymus to participate generally in cell-mediated immunity, and type 2 T helper cells (Th2) which participate in humoral immunity. Both of the T cell groups are known to keep each other in check, and atypical responses such as autoimmune response or hypersensitive response occur when the balance is broken in the groups.

In addition, new types of T cells such as immunoregulatory T cells (Tregs) or Th17 which can regulate immune responses are known in the art. Treg may adjust Th1 cell activities, and serves to suppress the function of abnormally activated immune cells and control an inflammatory response. On the other hand, the Th17 cells secrete IL-17, and serves to maximize signals for inflammatory responses so as to accelerate the progression of diseases. In recent years, as these Treg or Th17 cells have emerged as novel targets of therapeutic agents for treating an immune disease, much research on immunoregulatory therapeutic agents has been conducted (Wood, K. J. et al., Nat. Rev. Immunol. 12(6):417-430, 2012; Miossec, P. et al., Nat. Rev. Drug Discov. 11(10):763-776, 2012; Noack, M. et al., Autoimmun. Rev. 13(6):668-677, 2014).

In general, conventional immunosuppressive drugs that suppress T cells in a non-specific manner have a drawback in that it is difficult to last a therapeutic effect for a long period of time since they are accompanied by side effects such as cytotoxicity, infections caused by compromised immunity, diabetes, tremor, headache, diarrhea, hypertension, nausea, renal dysfunction, etc. Therefore, there have been attempts conducted to develop methods of co-administering or replacing immunosuppressive drugs having different mechanisms of action especially in the field of organ transplantation so as to reduce serious side effects and enhance an immunosuppressive therapeutic effect. However, there are no optimized combinations or therapies for co-administration of the immunosuppressive drugs.

Therefore, it is urgent to develop a novel immunosuppressive or immunomodulatory therapy capable of reducing the side effect of the conventional immunosuppressive drugs and improving the therapeutic effects and to screen novel immunosuppressive drug candidates which are safer and have few side effects.

SUMMARY OF THE INVENTION

Accordingly, the present inventors have conducted research on novel immunomodulatory agents that have few side effects and can show a lasting therapeutic effect, and confirmed that the co-administration of metformin and a calcineurin inhibitor-based immunosuppressive drug suppresses the secretion of inflammatory cytokines and induces a synergistic effect on immunosuppression and immunomodulation such as Treg cell activation, etc. Thus, the present inventors have first found that the metformin particularly has an effect of alleviating nephrotoxicity caused due to the side effects of the conventional immunosuppressive drug. Therefore, the present invention has been completed based on these facts.

Therefore, it is an object of the present invention to provide a composition for reducing nephrotoxicity caused by an immunosuppressive drug, which includes metformin or a pharmaceutically acceptable salt thereof as an active ingredient.

It is another object of the present invention to provide a pharmaceutical composition for preventing or treating an immune disease, which includes a calcineurin inhibitor and metformin or a pharmaceutically acceptable salt thereof as active ingredients.

It is still another object of the present invention to provide a pharmaceutically combined preparation for preventing or treating an immune disease, wherein:

(a) a calcineurin inhibitor and metformin or a pharmaceutically acceptable salt thereof are included at a weight ratio of 1:1 to 1:3,500, and (b) the calcineurin inhibitor and the metformin or pharmaceutically acceptable salt thereof are administered simultaneously, separately, or in a predetermined order.

To solve the above problems, according to an aspect of the present invention, there is provided a composition for reducing nephrotoxicity caused by an immunosuppressive drug, which includes metformin or a pharmaceutically acceptable salt thereof as an active ingredient.

According to another aspect of the present invention, there is provided a pharmaceutical composition for preventing or treating an immune disease, which includes a calcineurin inhibitor and metformin or a pharmaceutically acceptable salt thereof as active ingredients.

According to still another aspect of the present invention, there is provided a pharmaceutically combined preparation for preventing or treating an immune disease, wherein:

(a) a calcineurin inhibitor and metformin or a pharmaceutically acceptable salt thereof are included at a weight ratio of 1:1 to 1:3,500, and (b) the calcineurin inhibitor and the metformin or pharmaceutically acceptable salt thereof are administered simultaneously, separately, or in a predetermined order.

Hereinafter, the present invention will be described in detail.

The present invention provides a composition for reducing nephrotoxicity caused by an immunosuppressive drug, which includes metformin or a pharmaceutically acceptable salt thereof as an active ingredient.

The composition for reducing nephrotoxicity caused by the immunosuppressive drug according to the present invention may be a composition for reducing nephrotoxicity caused by the immunosuppressive drug, particularly an calcineurin inhibitor. More particularly, the composition may be a composition for reducing nephrotoxicity caused by cyclosporine or tacrolimus.

Among the immunosuppressive drugs currently used in the art, calcineurin inhibitor (CNI)-based immunosuppressive drugs have been most widely used since their introduction at 1970s because they particularly have good short-term prognosis in patients, thereby enabling the development in the field of organ transplantation. Calcineurin is a calcium- and calmodulin-dependent protein phosphatase that activates a transcription factor important for differentiation of T cells, that is, a nuclear factor of activated T cells, cytoplasmic (NFATc), by dephosphorylating the transcription factor. The NFATc activated by the calcineurin migrates into the cell nuclei to enhance the expression of interleukin 2 (IL-2), which then promotes the proliferation and differentiation of T cells. Representative examples of the CNI-based immunosuppressive drugs, which have an immunosuppressive effect by suppressing calcineurin important for the activation of T cells, include cyclosporine and tacrolimus.

Cyclosporine (ciclosporin or cyclosporin) is known as cyclosporine A (ciclosporin A or cyclosporin A: abbreviated as CsA or Cys), and was first found in the fungus *Tolypocladium inflatum*. Cyclosporine has a peptide consisting of 11 amino acids, and has the following chemical structure (Formula: $C_{62}H_{111}N_{11}O_{12}$, and Molecular weight: 1202.61). In particular, cyclosporine binds to cyclophilin that is an immunophilin protein expressed by lymphocytes such as T cells, and a complex of cyclosporine and cyclophilin then binds to calcineurin to suppress the phosphatase activity of calcineurin. Cyclosporine is circulating under the brand names "SANDIMMUNE," "NEORAL," etc., and its generic medicines are also being sold on the market.

<Structure of Cyclosporine>

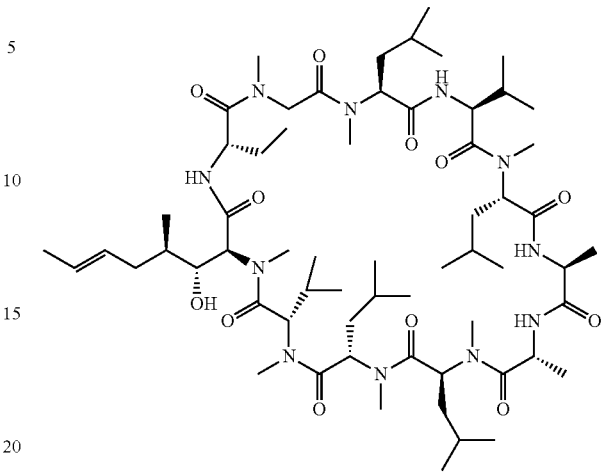

<Structure of Tacrolimus>

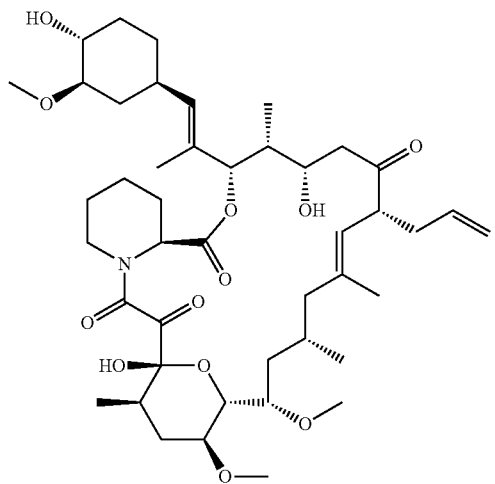 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

Tacrolimus is also known as FK506 (or FK-506), fujimycin, etc., and was found from the bacteria *Streptomyces tsukubaensis* which lives in the soil in Japan. Tacrolimus is a compound having a macrolide lactone structure, and thus has a structure as described above (Formula: $C_{44}H_{69}NO_{12}$, and Molecular weight: 804.02). Tacrolimus has a different chemical structure than cyclosporine, but has a very similar mechanism of action. That is, tacrolimus binds to an immunophilin protein, FKBP12, and a complex of tacrolimus and FKBP12 then binds to calcineurin to suppress the enzymatic activity of calcineurin. Tacrolimus is circulating under the brand names "Prograf," "Advagraf," "Astagraf XL," etc., and its generic medicines are also being sold on the market.

Since calcineurin is generally expressed in T cells of the immune system and also expressed in the other cells and tissues, an inhibitory action of cyclosporine or tacrolimus on calcineurin is accompanied with various side effects in addition to the immunosuppressive effect (Liu, E. H. et al., Nat. Immunol. 8(1):25-30, 2007). The side effects of the immunosuppressive drug have a serious effect on the long-term stable and successful organ transplantation and the patients' survival rate, and also have a big problem in treating diseases in addition to the problem regarding the organ transplantation requiring the immunosuppression. Among the side effects of the CNI-based immunosuppressive drugs, acute and chronic nephrotoxicity is of particular importance (Naesens, M. et al., Clin. J. Am. Soc. Nephrol. 4(2):481-508, 2009). The nephrotoxicity caused by the CNI-based immunosuppressive drugs is expressed due to a histological change in kidney such as generation of vacuoles in the renal tubules, interstitial fibrosis, arteriolar hyalinization, and the like, a decline in renal function such as a decrease in effective renal blood flow and glomerular filtration rate, etc.

Accordingly, the present invention provides a composition for reducing nephrotoxicity caused by an immunosuppressive drug, which includes metformin or a pharmaceutically acceptable salt thereof as an active ingredient. Here, the composition is able to alleviate the nephrotoxicity caused due to the side effects of the immunosuppressive drug, preferably a CNI-based immunosuppressive drug, thereby improving a lasting therapeutic effect of the immunosuppressive drug.

The present inventors have first found that metformin has an effect of alleviating nephrotoxicity caused by a CNI-based inhibitor (i.e., tacrolimus) in an animal model of nephrotoxicity caused by tacrolimus according to one exemplary embodiment. Specifically, an experimental group in which tacrolimus and metformin are co-administered has a statistically significantly improved index of kidney function, compared to a group in which tacrolimus is administered alone. Also, animal experiments show that another CNI-based immunosuppressive drug (i.e., cyclosporine) also caused damage to the kidney but improve the renal function when administered together with metformin.

Metformin is a biguanid-based compound having a structure represented by the following formula, particularly an anti-diabetic agent used to treat type 2 diabetes. Metformin is circulating under the trademark "Glucophage," and a variety of its generic medicines are also being sold on the market (Formula: $C_4H_{11}N_5$, and Molecular weight: 129.16).

<Structure of Metformin>

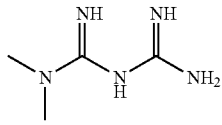

In the composition according to the present invention, metformin may be used by itself or in the form of a salt, preferably a pharmaceutically acceptable salt. In the present invention, the term "pharmaceutically acceptable" generally means that a salt is physiologically acceptable, and usually does not cause an allergic reaction or similar reactions when administered to humans. In this case, an acid addition salt formed by a pharmaceutically acceptable free acid is desirable as the salt. An organic acid and an inorganic acid may be used as the free acid. The organic acid includes citric acid, acetic acid, lactic acid, tartaric acid, maleic acid, fumaric acid, formic acid, propionic acid, oxalic acid, trifluoroacetic acid, benzoic acid, gluconic acid, metasulfonic acid, glycolic acid, succinic acid, 4-toluenesulfonic acid, glutamic acid, and aspartic acid, but the present invention is not limited thereto. Also, the inorganic acid includes hydrochloric acid, bromic acid, sulfuric acid, and phosphoric acid, but the present invention is not limited thereto.

In the composition according to the present invention, metformin or pharmaceutically acceptable salts thereof that are isolated from natural resources or prepared using chemical synthesis methods known in the related art may be used as the metformin compound or pharmaceutically acceptable salt.

Also, the present invention provides a pharmaceutical composition for preventing or treating an immune disease, which includes a calcineurin inhibitor and metformin or a pharmaceutically acceptable salt thereof as active ingredients.

The calcineurin inhibitor that is an active ingredient of the pharmaceutical composition according to the present invention may preferably include cyclosporine or tacrolimus.

The present inventors have found that a therapeutic effect through immunosuppression is further improved and side effects such as nephrotoxicity are alleviated when the immunosuppressive drug and metformin are administered at the same time. Thus, there is provided a pharmaceutical composition for preventing or treating an immune disease, which includes a calcineurin inhibitor and metformin or a pharmaceutically acceptable salt thereof as active ingredients.

In recent years, the present inventors have found and first reported that metformin has an effect of regulating the Treg/Th17 balance by suppressing Th17 cells and inducing the differentiation of Treg cells (Son, J. H. et al., Mediators Inflamm. volume 2014, Article ID 973986, 2014). According to one exemplary embodiment of the present invention, it was observed that metformin has an immunomodulatory effect on T cells, for example, by suppressing the proliferation of T cells and the secretion of cytokines under the conditions for an allogeneic immune response when treated alone. Further, the present inventors have found that metformin shows a superior synergistic effect on immunosuppression or immunomodulation when metformin and tacrolimus are treated together, compared to when metformin and tacrolimus are treated alone. In addition, the present inventors have confirmed through animal experiments provided in examples found that the nephrotoxicity caused by tacrolimus is reduced when tacrolimus and metformin are co-administered. A synergistic effect on the immunomodulation and an effect on improvement of nephrotoxicity, which have been achieved upon the co-administration of metformin and tacrolimus, are also observed upon the co-administration of metformin and cyclosporine. In particular, cyclosporine highly suppresses Treg cells serving to regulate inflammations when treated alone (see Example <5-2>), but has an effect of highly increasing a Treg level when co-administered with metformin.

In the pharmaceutical composition of the present invention, the metformin and the cyclosporine or tacrolimus may be used by themselves, or used in the form of a salt, preferably a pharmaceutically acceptable salt. The pharmaceutically acceptable salt is as described above.

In the pharmaceutical composition of the present invention, metformin and cyclosporine or tacrolimus that are isolated from natural resources or prepared using chemical synthesis methods known in the related art may be used as the metformin and the cyclosporine or tacrolimus.

A weight ratio of the calcineurin inhibitor and the metformin or pharmaceutically acceptable salt thereof included in the pharmaceutical composition of the present invention may be in a range of 1:1 to 1:3,500, preferably in a range of 1:5 to 1:500.

The pharmaceutical composition according to the present invention may include only a pharmaceutically effective amount of the calcineurin inhibitor and the metformin or pharmaceutically acceptable salt thereof, or may include a pharmaceutically acceptable carrier. The term "pharmaceutically effective amount" refers to an amount sufficient to cause a higher reaction compared to the negative control, preferably to an amount sufficient to have a synergistic effect on the immunosuppression and immunomodulation and alleviate nephrotoxicity caused by the calcineurin inhibitor when metformin is administered simultaneously with the calcineurin inhibitor to treat or prevent acute or chronic organ transplant rejection, an autoimmune disease or an inflammatory disease, particularly to an amount at which the calcineurin inhibitor and metformin are included at the weight ratio in the pharmaceutical composition.

A pharmaceutically effective amount of the calcineurin inhibitor included as the active ingredient in the pharmaceutical composition of the present invention is in a range of 1 to 5 mg/day/kg of body weight in the case of cyclosporine, in a range of 0.01 to 0.1 mg/day/kg of body weight in the case of tacrolimus, and in a range of 5 to 35 mg/day/kg of body weight in the case of metformin. However, the pharmaceutically effective amount may properly vary depending on various factors such as the diseases and its severity, the age, weight, health condition, and sex of a patient, a route of administration, and a treatment period.

The pharmaceutical composition of the present invention may be widely formulated with a pharmaceutically acceptable carrier through a route of administration using a method known in the art so as to have a synergistic effect on immunosuppression or immunomodulation upon co-administration of the calcineurin inhibitor and metformin. The term "pharmaceutically acceptable" refers to a non-toxic composition that is physiologically acceptable, does not hinder an action of the active ingredient and generally causes no allergic reaction or similar reactions such as gastrointestinal disturbance, dizziness, and the like when administered to humans. The carrier includes all types of solvents, dispersive media, oil-in-water or water-in-oil emulsions, aqueous compositions, liposomes, microbeads, and microsomes.

The route of administration may be an oral or parenteral route of administration. A parenteral administration method may include intravenous, intramuscular, intra-arterial, intramedullary, intradural, intracardiac, percutaneous, subcutaneous, intraperitoneal, intranasal, intestinal, local, sublingual or intrectal administration, but the present invention is not limited thereto.

When the pharmaceutical composition of the present invention is orally administered, the pharmaceutical composition of the present invention may be formulated with a proper carrier for oral administration into the form of a powder, a granule, a tablet, a pill, a sugar-coated tablet, a capsule, a liquid, a gel, syrup, a suspension, a wafer, etc. according to methods known in the related art. Examples of the proper carrier may include sugars including lactose, dextrose, sucrose, sorbitol, mannitol, xylitol, erythritol, maltitol, etc., starches including corn starch, wheat starch, rice starch, potato starch, etc., celluloses including cellulose, methyl cellulose, sodium carboxymethyl cellulose, hydroxypropyl methylcellulose, etc., fillers such as gelatin, polyvinyl pyrrolidone, etc. Also, cross-linked polyvinyl pyrrolidone, agar, alginic acid or sodium alginate, and the like may be added as a disintegrating agent, when necessary. Further, the pharmaceutical composition may further include an anti-agglomerating agent, a lubricant, a wetting agent, a flavoring agent, an emulsifying agent, a preservative, etc.

Also, when parenterally administered, the pharmaceutical composition of the present invention may be formulated with a proper carrier for parenteral administration into the form of an injectable solution, a percutaneous administration preparation, and a nasal inhaler preparation using methods known in the related art. The injectable solution should be essentially sterilized, and protected from being contaminated by microbes such as bacteria and fungi. In the case of the injectable solution, examples of the proper carrier may include a solvent or a dispersive medium such as water, ethanol, polyols (for example, glycerol, propylene glycol, liquid polyethylene glycol, etc.), a mixture and/or vegetable oil thereof, but the present invention is not limited thereto. More preferably, Hanks' solution, Ringer solution, triethanol amine-containing phosphate-buffered saline (PBS) or sterile water for injections, or an isotonic solution such as 10% ethanol, 40% propylene glycol, and 5% dextrose may be used as the proper carrier. The injectable solution may further include various antimicrobial and antifungal agents such as paraben, chlorobutanol, phenol, sorbic acid, thimerosal, and the like so as to protect the injectable solution from being contaminated by microbes. In most cases, the injectable solution may also further include an isotonic agent such as a sugar or sodium chloride.

The percutaneous administration preparation is included in the form of an ointment, a cream, a lotion, a gel, a liquid for external use, pasta, a liniment, an aerosol, etc. As such, the term "percutaneous administration" means that an effective amount of the active ingredient included in the pharmaceutical composition is delivered into the skin when the pharmaceutical composition is locally administered to the skin. For example, the pharmaceutical composition of the present invention may be administered using a method which includes preparing the pharmaceutical composition into an injectable formulation and gently pricking the skin to inject the injectable formulation with a fine syringe needle (30 gauges), or directly applying the pharmaceutical composition into onto the skin. These formulations are disclosed in Korean Patent Unexamined Publication No. 2010-0063827.

In the case of the inhaling administration preparation, the compound used according to the present invention may be readily delivered in the form of an aerosol spray from a pressurized pack or a fog machine using a proper propellant, for example, dichlorofluoromethane, trichlorofluoromethane, dichlorotetrafluoroethane, carbon dioxide, or other proper gases. The dosage of pressured aerosol may be determined by providing a valve through which an amount of calculated aerosol passes. For example, a gelatin capsule and a cartridge used in a nebulizer or an insufflator may be formulated to contain a powder mixture of a compound and a proper powder base such as lactose or starch.

In addition, the pharmaceutically acceptable carrier may refer to what is disclosed in the patent document (Korean Patent Unexamined Publication No. 2003-0007104).

Also, the pharmaceutical composition according to the present invention may further include one or more buffers (for example, saline or PBS), carbohydrates (for example, glucose, mannose, sucrose, or dextran), antioxidants, bacteriostatic agents, chelating agents (for example, EDTA or glutathione), adjuvants (for example, aluminum hydroxide), suspending agents, thickening agents, and/or preservatives.

In addition, the pharmaceutical composition of the present invention may be formulated using methods known in the related art so that the active ingredient may be released in an immediate, sustained or delayed manner after administered to a mammal.

Additionally, the pharmaceutical composition of the present invention may be administered in conjunction with known compounds having an effect of preventing or treating acute or chronic organ transplant rejection, an autoimmune disease, or an inflammatory disease.

The pharmaceutical composition of the present invention may be a pharmaceutical composition for preventing or treating an immune disease selected from the group consisting of acute or chronic organ transplant rejection, an autoimmune disease, and an inflammatory disease.

Therapeutic and prophylactic indications of the pharmaceutical composition of the present invention may particularly include acute or chronic transplant rejection caused after transplantation into the heart, the lung, a heart/lung composite, the liver, the kidney, the pancreas, the skin, bowels, or the cornea, and graft-versus-host diseases caused after bone marrow transplantation. In particular, the therapeutic and prophylactic indications may include post-transplantation rejection mediated by T cells.

Also, the therapeutic and prophylactic indications of the pharmaceutical composition of the present invention may include an autoimmune disease or an inflammatory disease. Specifically, examples of the therapeutic and prophylactic indications may be selected from the group consisting of septicemia, arteriosclerosis, bacteremia, systemic inflammatory response syndrome, multiple organ dysfunction syndrome, osteoporosis, periodontitis, systemic lupus erythematosus, rheumatoid arthritis, osteoarthritis, juvenile chronic arthritis, spondylarthropathy, multiple sclerosis, systemic sclerosis, idiopathic inflammatory myopathy, Sjogren's syndrome, systemic angiitis, sarcoidosis, autoimmune hemolytic anaemia, autoimmune thrombocytopenia, thyroiditis, diabetes mellitus, immune-mediated renal disease, a demyelinating disease of the central and peripheral nervous systems, idiopathic demyelinating multiple neuritis, Guillain-Barre syndrome, chronic inflammatory demyelinating multiple neuritis, a hepatobiliary disease, infectiousor autoimmune chronic active hepatitis, primary biliary cirrhosis, granulomatous hepatitis, sclerosing cholangitis, inflammatory bowel disease (IBD), ulcerative colitis, Crohn's disease, irritable bowel syndrome, gluten-sensitive enteropathy, Whipple's disease, an autoimmune or immune-mediated skin disease, a bullous skin disease, erythema multiforme, contact dermatitis, psoriasis, an allergic disease, asthma, allergic rhinitis, atopic dermatitis, food hypersensitivity, acne, urticaria, an immunologic disease of the lung, eosinophilic pneumonia, idiopathic pulmonary fibrosis, hypersensitivity pneumonitis, etc.

Also, the present invention provides a pharmaceutically combined preparation for preventing or treating an immune disease, wherein:

(a) a calcineurin inhibitor and metformin or a pharmaceutically acceptable salt thereof are included at a weight ratio of 1:1 to 1:3,500, and (b) the calcineurin inhibitor and the metformin or pharmaceutically acceptable salt thereof are administered simultaneously, separately, or in a predetermined order.

The pharmaceutically combined preparation of the present invention may include a calcineurin inhibitor and metformin as constituent elements. Here, the calcineurin inhibitor may preferably include cyclosporine or tacrolimus.

Tacrolimus or cyclosporine and metformin that are the constituent elements in the pharmaceutically combined preparation of the present invention may be used by themselves, or used in the form of a salt, preferably a pharmaceutically acceptable salt. As such, the term "pharmaceutically acceptable" is as described above.

The pharmaceutically combined preparation of the present invention may be formulated, depending on an administration method and a route of administration, so that the calcineurin inhibitor and metformin are included as the constituent elements in one formulation, or the calcineurin inhibitor and the metformin may be separately formulated, depending on the daily dosage or once dosage, so that the calcineurin inhibitor and the metformin can be included in one package. The formulations of the separately formulated calcineurin inhibitor and metformin may be or may not be identical. A specific method of formulating the pharmaceutically combined preparation of the present invention and a pharmaceutically acceptable carrier that may be included in the formulation are as described above for the pharmaceutical composition of the present invention disclosed in the other section of this specification, may refer to what is disclosed in the patent document (Korean Patent Unexamined Publication No. 2003-0007104).

The term "pharmaceutically effective amount" refers to an amount sufficient to cause a higher reaction compared to the negative control, preferably to an amount sufficient to have a synergistic effect on the immunosuppression and immunomodulation and alleviate nephrotoxicity caused by the calcineurin inhibitor when the calcineurin inhibitor and metformin of the pharmaceutically combined preparation according to the present invention are co-administered so as to treat or prevent acute or chronic organ transplant rejection, an autoimmune disease or an inflammatory disease. Also, the pharmaceutically effective amount means that the calcineurin inhibitor and metformin are included at a weight ratio of 1:1 to 1:3,500 as the constituent elements in a dosage of the pharmaceutically combined preparation.

Therefore, a dose of the calcineurin inhibitor that is the constituent element in the pharmaceutically combined preparation of the present invention may be in a range of 1 to 5 mg/day/kg of body weight in the case of the cyclosporine, in a range of 0.01 to 0.1 mg/day/kg of body weight in the case of the tacrolimus, and in a range of 5 to 35 mg/day/kg of body weight in the case of the metformin or pharmaceutically acceptable salt thereof.

The route of administration of the pharmaceutically combined preparation according to the present invention may be an oral or parenteral route of administration. For example, the parenteral route of administration includes various routes such as percutaneous, intranasal, intraperitoneal, intramuscular, subcutaneous or intravenous administration, but the present invention is not limited thereto. The routes of administration of the separately formulated calcineurin inhibitor and metformin may be or may not be identical.

As the constituent elements in the pharmaceutically combined preparation of the present invention, the calcineurin inhibitor and metformin may be administered simultaneously, separately, or in a predetermined order. The term "simultaneously administered" means that two constituent elements are present at the same time in the stomach when orally administered since the calcineurin inhibitor and metformin are ingested together or at substantially the same time (for example, an administration time interval of 15 minutes or less). When administered simultaneously, the calcineurin inhibitor and metformin may be formulated so that the calcineurin inhibitor and metformin can be included together in one package. For oral administration, the calcineurin inhibitor and metformin may be preferably formulated so that all daily doses are included in a once dose, and also be formulated so that the calcineurin inhibitor and metformin are administered 2, 3 and 4 times a day in divided doses.

The preferred dose of the pharmaceutically combined preparation according to the present invention may properly vary depending on various factors such as the diseases and its severity, the age, weight, health condition, and sex of a patient, a route of administration, and a treatment period. Since there is a difference in bioavailability of the calcineurin inhibitor and metformin between individuals, it may be preferred that a blood concentration of each drug is determined using an assay based on monoclonal antibodies, etc. known in the related art at the initial stage of administration of the pharmaceutical preparation according to the present invention.

The pharmaceutically combined preparation of the present invention may be a pharmaceutical composition for preventing or treating an immune disease selected from the group consisting of acute or chronic organ transplant rejection, an autoimmune disease, and an inflammatory disease.

Specific examples of the therapeutic and prophylactic indications of the pharmaceutically combined preparation according to the present invention are identical to specific examples of the therapeutic and prophylactic indications of the pharmaceutical composition of the present invention disclosed in the other section of this specification.

Also, the present invention provides a method of preventing or treating nephrotoxicity caused by an immunosuppressive drug, which includes:

1) selecting a subject with nephrotoxicity caused by an immunosuppressive drug; and
2) administering metformin or a pharmaceutically acceptable salt thereof to the subject.

The immunosuppressive drug may be a calcineurin inhibitor. Preferably, the calcineurin inhibitor may include cyclosporine or tacrolimus.

Further, the present invention provides a method of preventing or treating an immune disease, which includes:

administering a calcineurin inhibitor and metformin or a pharmaceutically acceptable salt thereof to a subject with an immune disease.

The calcineurin inhibitor may include cyclosporine or tacrolimus.

The calcineurin inhibitor and the metformin or pharmaceutically acceptable salt thereof are included at a weight ratio of 1:1 to 1:3,500, preferably a weight ratio of 1:5 to 1:500.

A daily dose of the cyclosporine may be in a range of 1 to 5 mg/day/kg of body weight, a daily dose of the tacrolimus may be in a range of 0.01 to 0.1 mg/day/kg of body weight, and a daily dose of the metformin or pharmaceutically acceptable salt thereof may be in a range of 5 to 35 mg/day/kg of body weight.

The immune disease may be selected from the group consisting of acute or chronic organ transplant rejection, an autoimmune disease, and an inflammatory disease.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 8A is a scatter plot, and FIG. 8B shows a percentage (%) of Foxp3+CD25+ cells. * represents a statistical significance;

FIG. 9A is a scatter plot, and FIG. 9B shows a percentage (%) of the Foxp3+CD25+ cells. * represents a statistical significance;

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclatures used in this specification and the experimental methods described below are widely known and generally used in the related art.

EXAMPLE 1

Effect of Metformin on Nephrotoxicity Caused by Calcineurin Inhibitor

<1-1> Effect of Metformin on Nephrotoxicity Caused by FK506

Figure 1A:
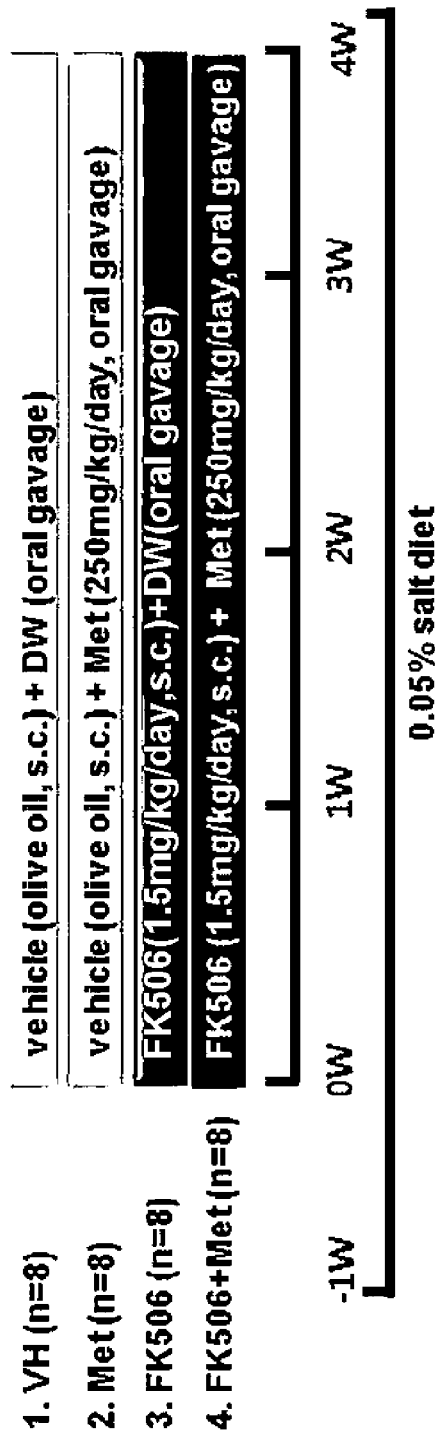
FIG. 1A is a diagram showing an overview of an animal experiment for determining an effect of metformin on nephrotoxicity caused by FK506 in rats.

A renal protective effect of metformin in an animal model of nephrotoxicity caused by FK506 (tacrolimus) was examined. A 0.05% low salt diet and the drug were administered to Sprague-Dawley rats weighing 200 to 220 g for a total of 4 weeks according to the experimental overview shown in FIG. 1A, and the indices of kidney function in blood were compared. The rats were divided into a total of four groups: a vehicle-treated group (VH) as the negative control, a group (FK506) in which FK506 was administered alone, a group (Met) in which metformin was administered alone, and a co-administered group (FK506+Met), with eight rats in each group.

FK506 dissolved in olive oil was subcutaneously (s.c.) injected once a day at a dose of 1.5 mg/kg of body weight to the experimental groups in which FK506 was administered, that is, a group in which FK506 was administered alone and a co-administered group, and an equivalent amount of olive oil was administered to the experimental groups in which FK506 was not administered, that is, a VH group and a group in which metformin was administered alone using the same method. Metformin dissolved in distilled water was orally administered (oral gavage) once a day at a dose of 250 mg/kg of body weight to the experimental groups in which metformin was administered, that is, a group in which metformin was administered alone and a co-administered group, and an equivalent amount of distilled water (DW) was administered to the groups in which metformin was not administered, that is a VH group and a group in which FK506 was administered alone using the same method.

After 4 weeks of drug administration, the body weights of the rats in each group were measured, and the animals were sacrificed to collect whole blood. Thereafter, a blood concentration of FK506 in the collected whole blood was measured using a mass spectrometer (API 3000 LC/MS/MS, Applied Biocystem, Foster City, Calif.). Then, the indices of kidney function, that is, serum creatinine (Scr) and blood urea nitrogen (BUN) levels in the sera obtained by centrifuging the collected blood were measured (Cobas analyzer, Roche Diagnostics, Montclair, N.J.). The data were expressed as average±standard error, and the statistical analysis was carried out by performing a Kruskal-Wallis test using a statistical package for the Social Sciences version 9.0 (SPSS; Chicago, Ill.), followed by performing an analysis of variance (ANOVA) using a Turkey or Dunnett test to calculate a Pearson's correlation coefficient. The criterion of statistical significance was $p<0.05$.

Figure 1B:
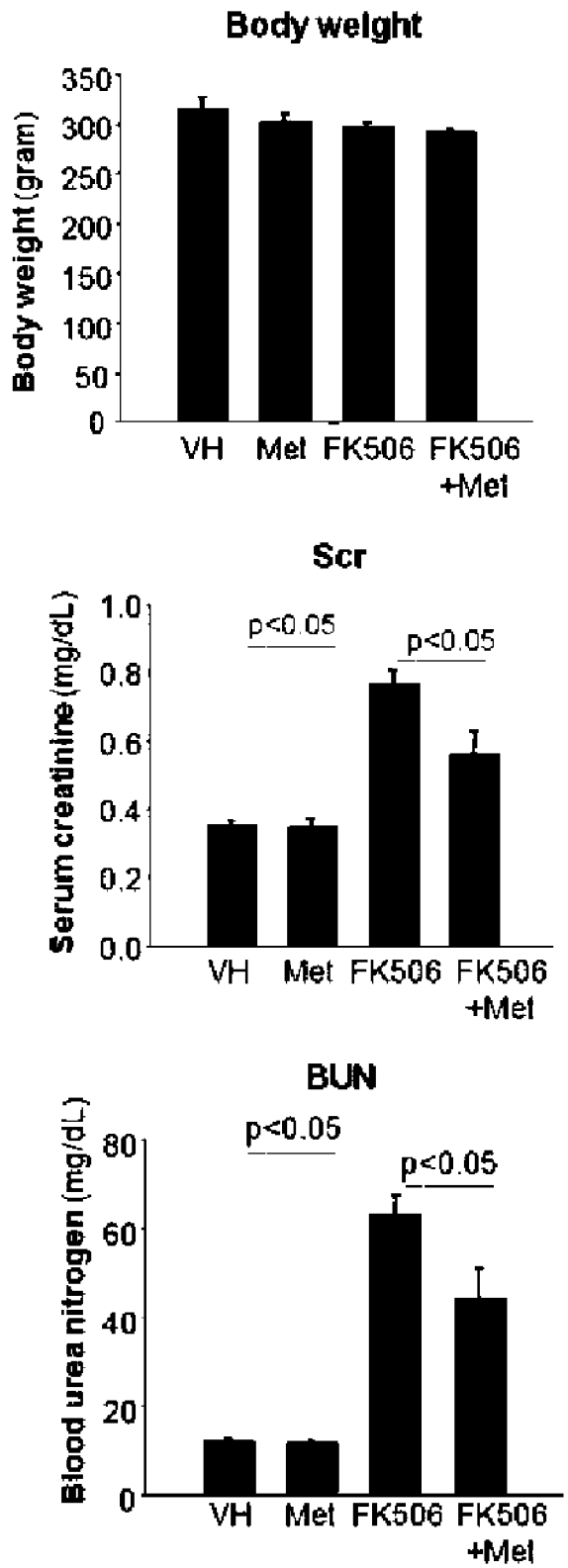
FIG. 1B is a diagram showing body weights and levels of serum creatinine (Scr) and blood urea nitrogen (BUN) of the control and experimental groups, as measured after a drug is administered for 4 weeks.

There was no statistically significant difference in body weights of the rats in each of the drug-administered groups and the control measured after 4 weeks of experimentation (see FIG. 1B: 315.5±11.7 g in the case of the VH group; 303.17±8.4 g in the case of the group in which metformin was administered alone; 297.11±5.9 g in the case of the group in which FK506 was administered alone; and 292.33±3.6 g in the case of the co-administered group).

From the results of measurement of the indices of kidney function, it can be seen that, since both of serum creatinine (Scr) and blood urea nitrogen (BUN) had similar values in the VH group and the group in which metformin was administered alone (see FIG. 1B: 0.35±0.02 mg/dL for Scr in the case of the VH group; 0.35±0.03 mg/dL in the case of the group in which metformin was administered alone; and $p>0.05$ in the VH group vs. the group in which metformin was administered alone; and 12.2±0.7 mg/dL for BUN in the case of the VH group; 11.6±0.7 mg/dL in the case of the group in which metformin was administered alone; and $p>0.05$ in the VH group vs. the group in which metformin was administered alone), metformin did not cause nephrotoxicity when administered alone. On the other hand, it can be seen that, since both of the Scr and BUN dramatically increased to a statistically significant level in the group in which FK506 was administered alone (0.76±0.04 mg/dL for Scr in the case of the group in which FK506 was administered alone; and $p<v0.05$ in the group in which FK506 was administered alone vs. the VH group; and 63.1±5.3 mg/dL for BUN in the case of the group in which FK506 was administered alone; and $p<0.05$ in the group in which FK506 was administered alone vs. the VH group), compared to the VH group as the control, FK506 caused nephrotoxicity when administered alone, as known in the related art.

Meanwhile, it was revealed that both of the Scr and BUN dramatically decreased to a statistically significant level in the co-administered group (0.56±0.07 mg/dL for Scr in the case of the co-administered group; and $p<0.05$ in the co-administered group vs. the group in which FK506 was administered alone; and 44.4±6.9 mg/dL for BUN in the case of the co-administered group; $p<0.05$ in the co-administered group vs. the group in which FK506 was administered alone), compare to the group in which FK506 was administered alone. That is, it was revealed that the co-administered group had better renal functions, compared to the group in which FK506 was administered alone. The above results showed that metformin had a therapeutic effect on a decline in renal function by alleviating nephrotoxicity caused by FK506 when metformin was co-administered with FK506.

Further, the above results suggested that, since the blood FK506 concentrations did not differ greatly between the group in which FK506 was administered alone and the co-administered group (10.2±1.3 ng/mL in the case of the group in which FK506 was administered alone; and 10.7±0.9 ng/mL in the case of the co-administered group), metformin did not hinder the pharmacokinetics of FK506 in the co-administered group.

<1-2> Effect of Metformin on Nephrotoxicity Caused by Cyclosporine

Figure 2A:
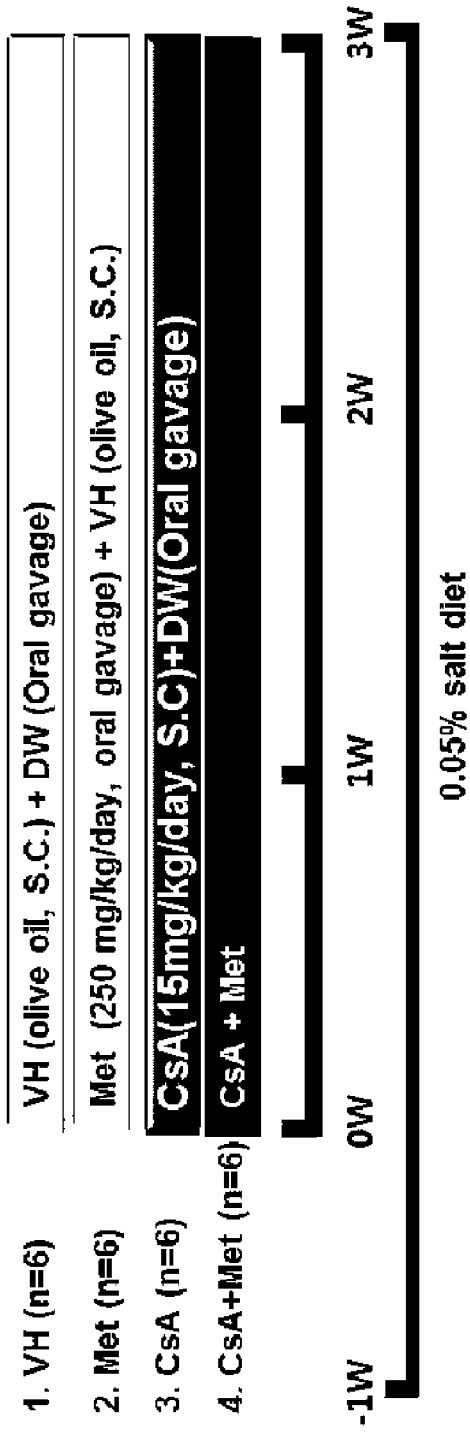
FIG. 2A is a diagram showing an overview of an animal experiment for determining an effect of metformin on nephrotoxicity caused by CsA in rats.

A renal protective effect of metformin in an animal model of nephrotoxicity caused by cyclosporine was examined. A 0.05% low salt diet and the drug were administered to Sprague-Dawley rats weighing 200 to 220 g for a total of 3 weeks according to the experimental overview shown in FIG. 2A, and the indices of kidney function in blood were compared. The rats were divided into a total of four groups: a vehicle-treated group (VH) as the negative control, a group (CsA) in which cyclosporine was administered alone, a group (Met) in which metformin was administered alone, and a co-administered group (CsA+Met), with six rats in each group.

CsA dissolved in olive oil was subcutaneously injected once a day at a dose of 15 mg/kg of body weight to the experimental groups in which CsA was administered, that is, a group in which CsA was administered alone and a co-administered group, and an equivalent amount of olive oil was administered to the experimental groups in which CsA was not administered, that is, a VH group and a group in which metformin was administered alone using the same method. Metformin dissolved in distilled water (DW) was orally administered (oral gavage) once a day at a dose of 250 mg/kg of body weight to the experimental groups in which metformin was administered, that is, a group in which metformin was administered alone and a co-administered group, and an equivalent amount of distilled water was administered to the groups in which metformin was not administered, that is a VH group and a group in which CsA was administered alone using the same method.

After 3 weeks of drug administration, the body weights of the rats in each group were measured, the animals were sacrificed to collect whole blood, and the collected whole blood was then centrifuged to obtain serum. Thereafter, the indices of kidney function, that is, serum creatinine (Scr) and blood urea nitrogen (BUN) levels in the sera were measured and statistically analyzed in the same manner as in Example <1-1>. The data were expressed as average±standard error, and the criterion of statistical significance was $p<0.05$.

Figure 2B:
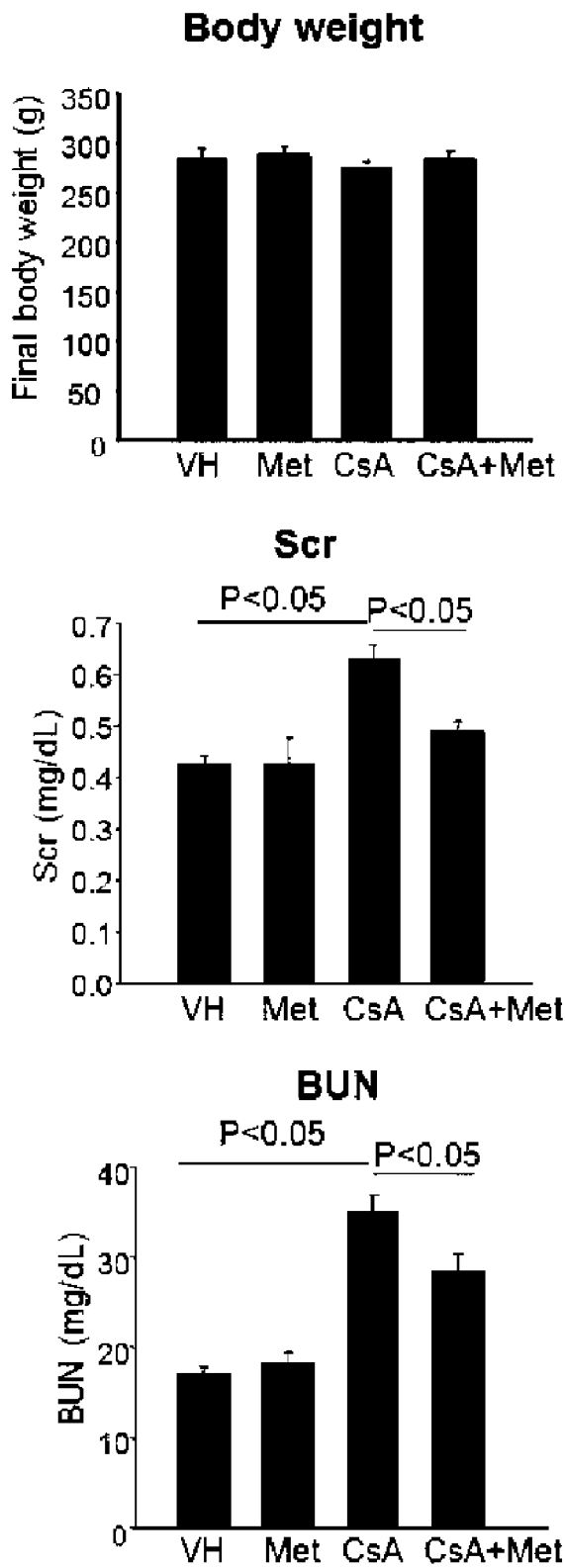
FIG. 2B is a diagram showing body weights and levels of serum creatinine (Scr) and blood urea nitrogen (BUN) of the control and experimental groups, as measured after a drug is administered for 3 weeks.

There was no statistically significant difference in body weights of the rats in each of the drug-administered groups and the control measured after 3 weeks of experimentation (see FIG. 2B: 283.0±9.8 g in the case of VH; 288.0±6.1 g in the case of Met; 275.0±4.3 g in the case of CsA; and 283.0±6.8 g in the case of CsA+Met).

From the results of measurement of the indices of kidney function, it was again confirmed that, since both of the Scr and BUN had similar values in the VH group and the group in which metformin was administered alone (FIG. 2B), metformin did not cause nephrotoxicity when administered alone. On the other hand, it can be seen that, since a level of Scr remarkably increased (0.63±0.03 mg/dL in the case of CsA; 0.43±0.01 mg/dL in the case of VH; and $p<0.05$ in CsA vs. VH) and a level of BUN also remarkably increased (35.2±1.8 mg/dL in the case of CsA; 17.0±0.8 mg/dL in the case of VH; and $p<0.05$ in CsA vs. VH) in the group in which CsA was administered alone, compared to the VH group as the control, the renal function was damaged when CsA was administered.

Meanwhile, it was revealed that the level of Scr decreased to a statistically significant level (0.49±0.02 mg/dL in the case of CsA+Met; and $p<0.05$ in CsA+Met vs. CsA) and the level of BUN remarkably decreased (28.7±1.7 mg/dL in the case of CsA+Met; and $p<0.05$ in CsA+Met vs. CsA) in the co-administered group, compared to the group in which CsA was administered alone. The above results showed that the renal functions of the co-administered group were further improved, compared to the group in which CsA was administered alone, and that metformin alleviated nephrotoxicity caused by CsA and had a therapeutic effect on a decline in renal function when metformin was co-administered with CsA.

EXAMPLE 2

Effect of Co-Administration of Metformin on Proliferation of Allogeneic Reactive T Cells <2-1> Metformin and FK506

Figure 3:
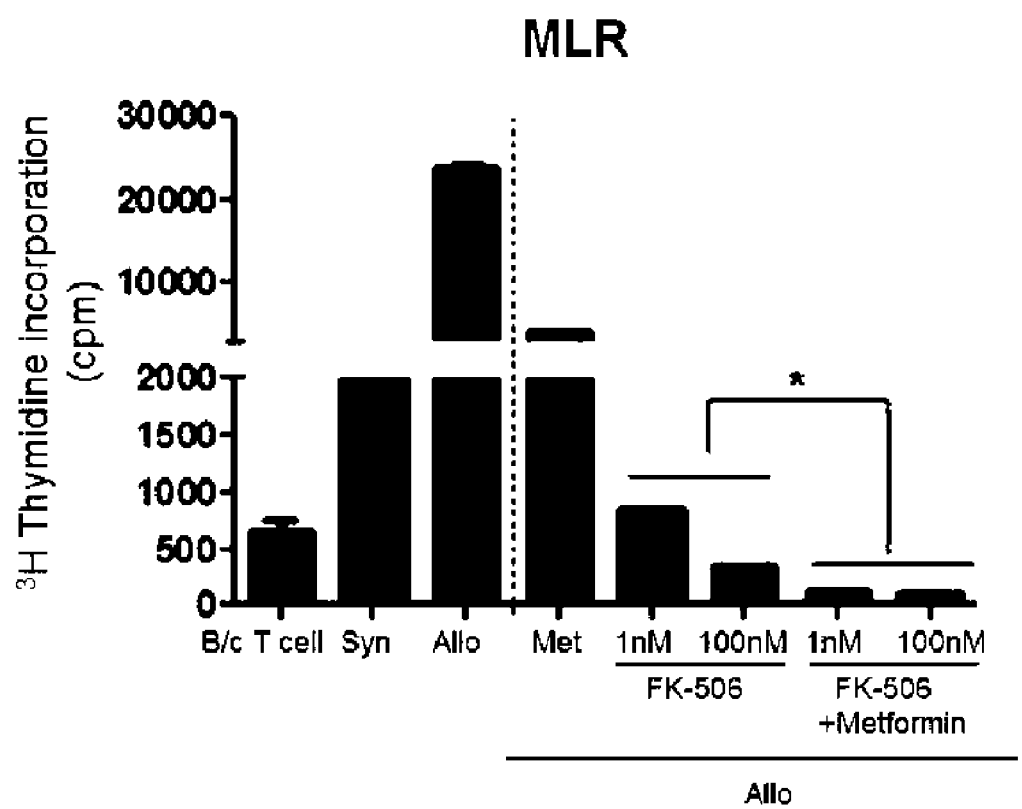
FIG. 3 is a diagram showing an effect of metformin and FK506 on proliferation of allogeneic reactive T cells in a mixed lymphocyte culture test (MLR). * represents a statistical significance.

To examine an immunomodulatory effect when T cells were co-treated with metformin and FK506 under in vitro allo-response conditions, an effect of metformin and FK506 on the proliferation of allogeneic reactive T cells was examined using a mixed lymphocyte culture method (i.e., a mixed lymphocyte reaction (MLR)) (FIG. 3). For the mixed lymphocyte culture, first, CD4+ T cells of a normal recipient (Balb/c, responder), and recipient (syngeneic)- or donor (C57BL/6, stimulator, allogeneic)-derived T cell-free splenocytes exposed to the radiation respectively were added in vitro into wells of a 96-well round bottom plate at a density of $2 \times 10^5$ cells/well, mixed, and then cultured. In this case, the T cells were treated separately or together with metformin (200 μM) or FK506 (1 nM or 100 nM) according to the experimental conditions, and then cultured for 3 days to stimulate an allogeneic response. On the last day of culture, [$^3$H]-thymidine was added, and the T cells were additionally cultured for 18 hours. Then, a level of [$^3$H]-thymidine uptake was measured using a liquid scintillation counter (Beckman, USA), and expressed as a cpm value. The statistical analysis was carried out using a Graph prism (t-test, ANOVA), and the statistical significance was $p<0.05$.

As a result, it was confirmed that the proliferation of T cells was suppressed when the T cells were treated with metformin alone (FIG. 3, Met), compared to the control (untreated Allo), and the proliferation of T cells was remarkably reduced in a concentration-dependent manner even when the T cells were treated with FK506 alone (FK-506). On the other hand, it was revealed that a combination of FK506 and metformin had a superior, statistically significant inhibitory effect on the proliferation of T cells when the T cells were treated together with FK506 and metformin (FK-506+Metformin), compared to when the T cells were treated with metformin or FK506 alone at the same concentration. That is, it can be seen that, when the T cells were co-treated with metformin and FK506 under the experimental conditions for mixed lymphocyte culture cells, an inhibitory effect of each of metformin and FK506 on the proliferation of T cells was able to be maximized.

<2-2> Metformin and Cyclosporine

Figure 4:
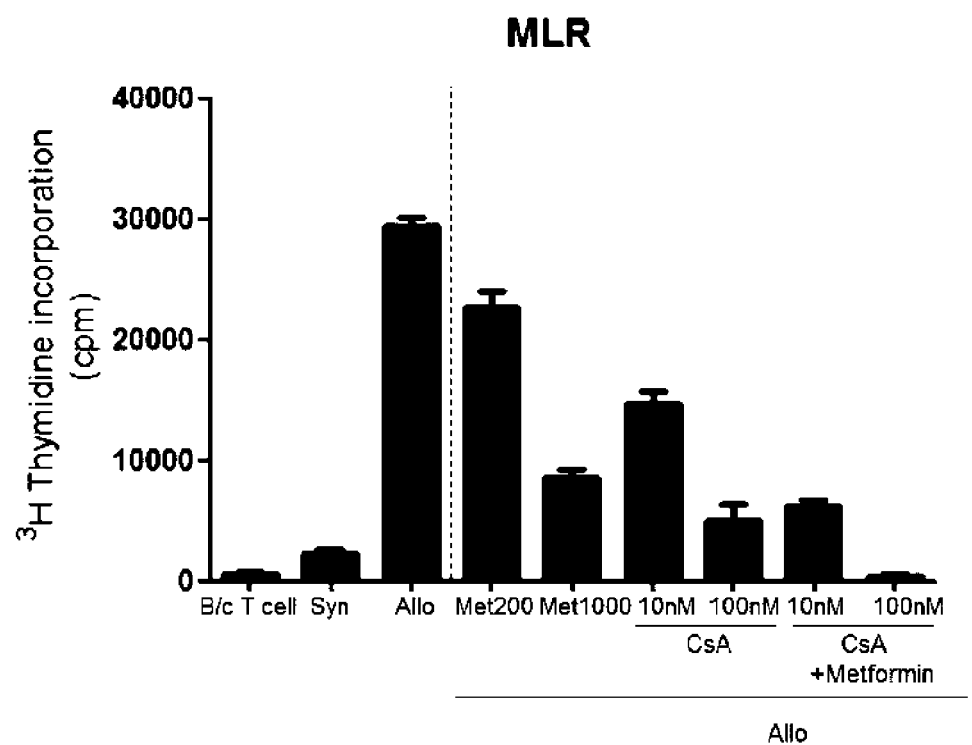
FIG. 4 is a diagram showing an effect of metformin and CsA on the proliferation of allogeneic reactive T cells in the mixed lymphocyte culture test (MLR)

To examine an immunomodulatory effect when T cells were co-treated with metformin and cyclosporine (CsA) under in vitro allo-response conditions, an effect of metformin and CsA on the proliferation of allogeneic reactive T cells was examined in the same manner as in Example <2-1> using a mixed lymphocyte culture method (MLR) (FIG. 4).

Similar to the results observed in Example <2-1>, it was confirmed that the proliferation of T cells was suppressed when the T cells were treated with metformin alone (FIG. 4, Met at 200 μM or 1,000 μM), compared to the control (untreated Allo), and the proliferation of T cells was remarkably reduced in a concentration-dependent manner even when the T cells were treated with CsA alone (CsA at 10 nM or 100 nM). On the other hand, it was revealed that a combination of CsA and metformin had a superior inhibitory effect on the proliferation of T cells when the T cells were treated together with CsA and metformin (CsA+Metformin; a concentration of co-administered metformin: 200 μM), compared to when the T cells were treated with metformin or CsA alone at the same concentration. These results showed that, when the T cells were co-treated with metformin and CsA under the experimental conditions for mixed lymphocyte culture cells, an inhibitory effect of each of metformin and CsA on the proliferation of T cells was able to be maximized.

EXAMPLE 3

Effect of Co-Administration of Metformin on Secretion Rate of Inflammatory Cytokines of T Cells <3-1> Metformin and FK506

Figure 5:
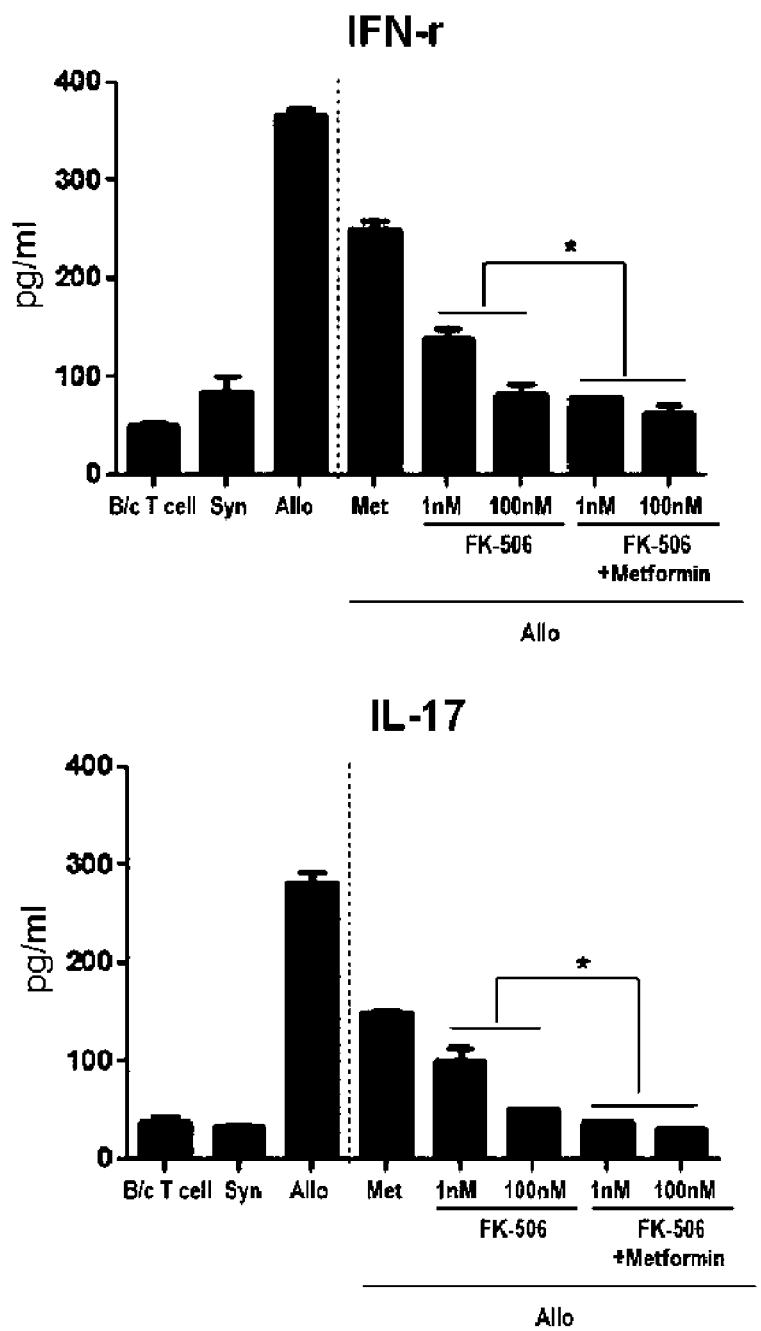
FIG. 5 shows experimental results of an enzyme-linked immunosorbent assay (ELISA) showing an effect of metformin and FK506 on secretion rates of inflammatory cytokines IFN-$\gamma$ and IL-17 secreted by the allogeneic reactive T cells in the mixed lymphocyte culture test. * represents a statistical significance.

To examine an effect of metformin and FK506 on the secretion of inflammatory cytokines by allogeneic reactive T cells, the allogeneic reactive T cells were treated with metformin (200 μM) or FK506 (1 nM or 100 nM) according to the experimental conditions, and then cultured for 3 days under the same in vitro allo-response conditions as in <Example 2>. Thereafter, levels of IFN-γ and IL-17 secreted by the T cells in the resulting culture broth were measured using ELISA (FIG. 5). The statistical analysis was carried out using a Graph prism (t-test, ANOVA), and the statistical significance was $p<0.05$.

As a result, a synergistic effect on the suppression of secretion of the inflammatory cytokines was observed when the T cells were co-treated with metformin and FK506. The concentrations of IFN-γ and IL-17 in the culture broth were reduced when the T cells were treated with metformin (FIG. 5, Met) or FK506 (FK-506) alone, whereas the concentrations of IFN-γ and IL-17 were more remarkably reduced when the T cells were co-treated with metformin and FK506 (FK-506+Metformin). That is, it can be seen that the inflammatory cytokines secreted by the T cells were able to be more effectively suppressed when the T cells were co-treated with metformin and FK506 under the experimental conditions for mixed lymphocyte culture cells.

<3-2> Metformin and Cyclosporine

Figure 6:
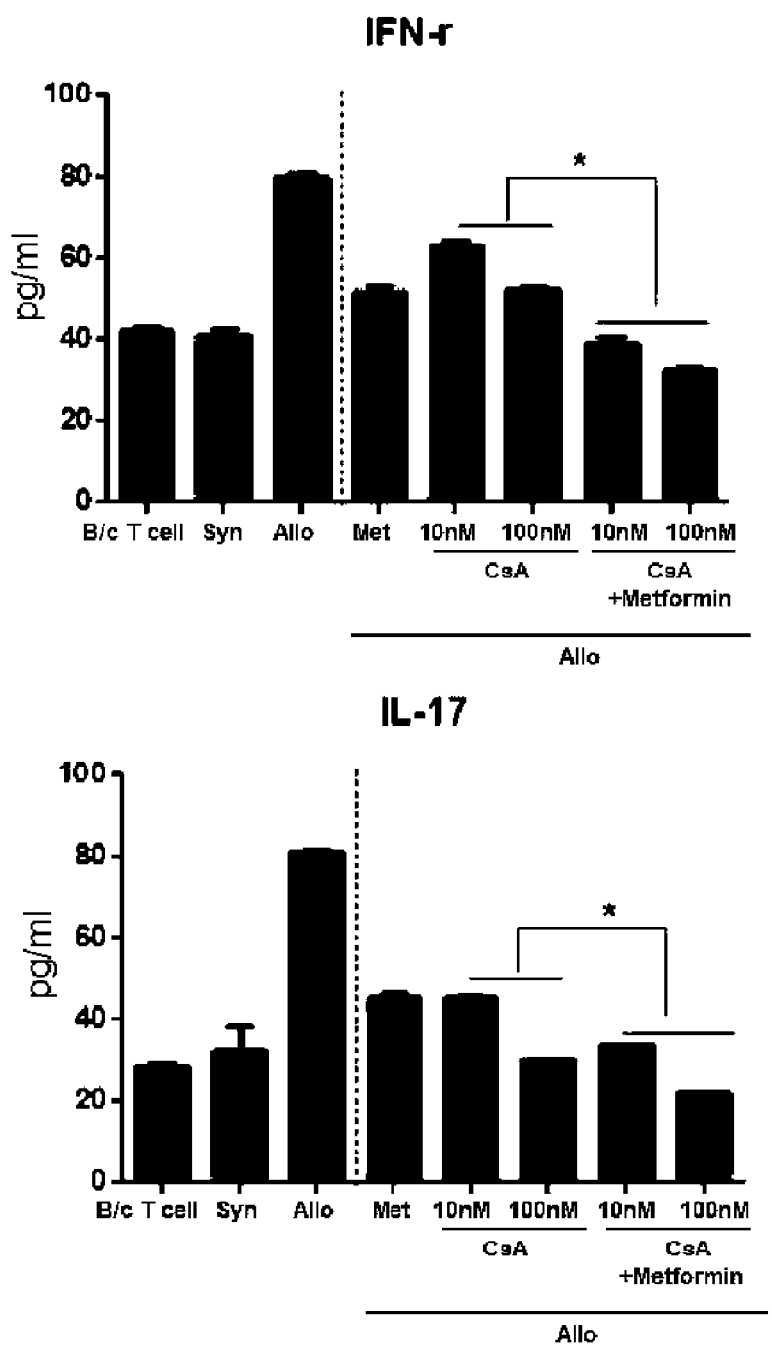
FIG. 6 shows ELISA experimental results showing an effect of metformin and CsA on secretion rates of the inflammatory cytokines IFN-$\gamma$ and IL-17 secreted by the allogeneic reactive T cells in the mixed lymphocyte culture test. * represents a statistical significance.

To examine an effect of metformin and cyclosporine (CsA) on the secretion of inflammatory cytokines by allogeneic reactive T cells, the allogeneic reactive T cells were treated with metformin (200 μM) or CsA (10 nM or 100 nM) according to the experimental conditions, and then cultured for 3 days under the in vitro allo-response conditions in the same manner as in Example <3-1>. Thereafter, levels of IFN-γ and IL-17 secreted by the T cells in the resulting culture broth were measured using ELISA (FIG. 6). The statistical analysis was carried out using a Graph prism (t-test, ANOVA), and the statistical significance was $p<0.05$.

Similar to the case in which metformin was co-administered with FK506, a synergistic effect on the suppression of secretion of inflammatory cytokines was observed even when the T cells were co-treated with metformin and CsA. The concentrations of IFN-γ and IL-17 secreted in the culture broth were reduced when the T cells were treated with metformin (FIG. 6, Met) or cyclosporine (CsA) alone, compared to the control, whereas the concentrations of IFN-γ and IL-17 were more remarkably reduced when the T cells were co-treated with metformin and CsA (CsA+Metformin). That is, it can be seen that the inflammatory cytokines secreted by the T cells were able to be more effectively suppressed when the T cells were co-treated with metformin and CsA under the experimental conditions for mixed lymphocyte culture cells.

EXAMPLE 4

Cytotoxicity Experiment Under T Cell Activation Conditions

Figure 7:
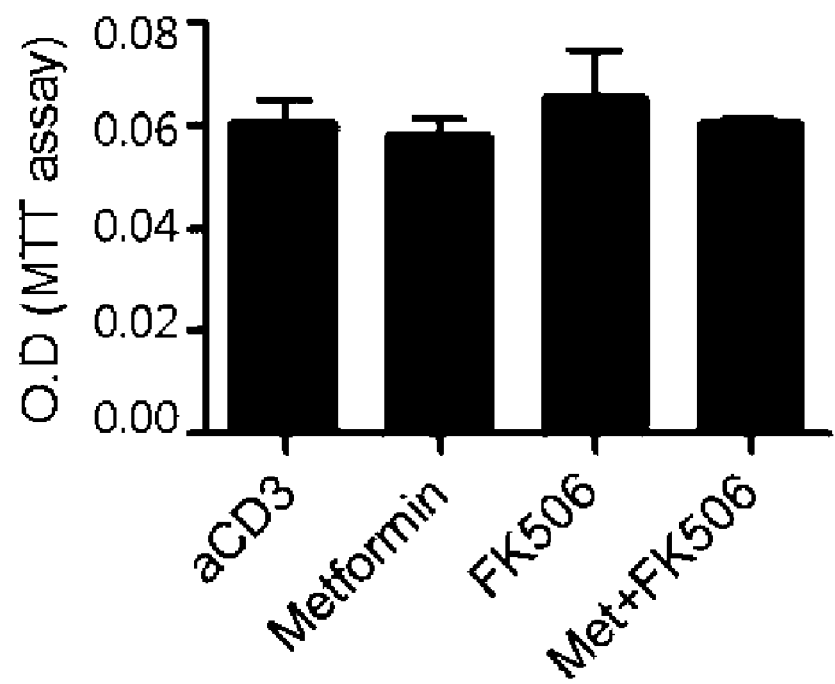
FIG. 7 shows experimental results of an MTT assay showing whether metformin and FK506 shows cytotoxicity under T cell activation conditions for using a CD3 antibody.

To determine whether the metformin and calcineurin inhibitor had non-specific cytotoxicity, an MTT assay was carried out under T cell activation conditions (anti-CD3 conditions) (FIG. 7). Splenocytes obtained from normal C57BL/6 mice were seeded in a 96-well plate at a density of $2\times10^5$ cells/ml, treated with metformin (200 μM) or FK506 (100 nM) according to the experimental conditions, and then cultured for 3 days under anti-CD3 activation conditions (1 μg/ml). In the MTT assay, a 3-(4,5dimethyl-thiazol-2-yl)-2,5-diphenyltetrazolium bromide compound was added before 4 hours of cell harvesting, and reacted for 4 hours. Thereafter, each well was treated with DMSO to measure the optical density at a wavelength of 540 nm.

As a result, it was revealed that there was no big difference in optical densities when the T cells were either treated with metformin (FIG. 7, Metformin) or FK506 (FK506) or co-treated with metformin and FK506 (Met+FK506), compared to the control (aCD3). Therefore, it was confirmed that metformin and FK506 had no cytotoxicity caused due to the drug treatment.

EXAMPLE 5

Effect of Co-Administration of Metformin on Activity of Treg Cells

<5-1> Metformin and FK506

Figure 8A:
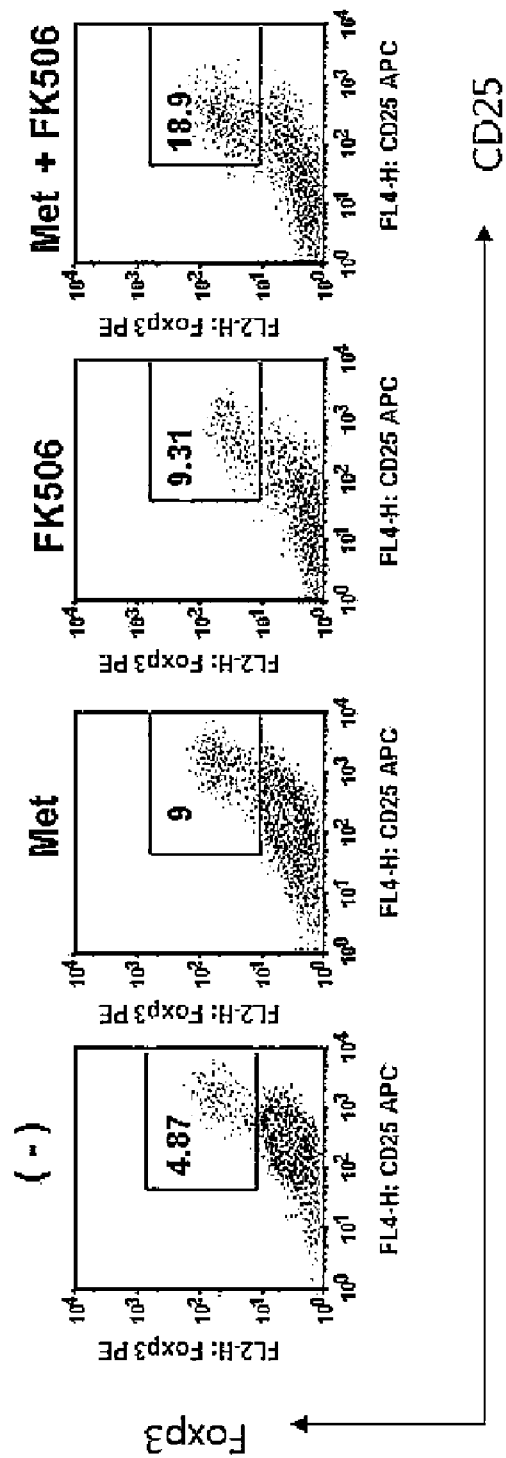
FIGS. 8A and 8B show experimental results of flow cytometry (FACS) showing an effect of metformin and FK506 on activities of Treg cells under the T cell activation conditions using the CD3 antibody.
Figure 8B:
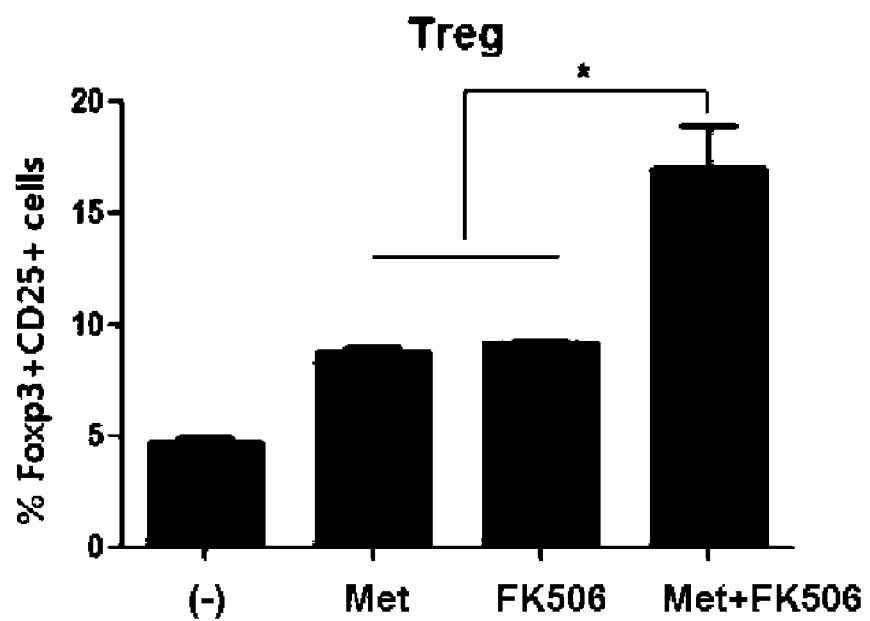

An effect of metformin and FK506 on the activity of Treg cells under T cell activation conditions (anti-CD3 conditions) was examined (FIGS. 8A and 8B). Splenocytes obtained from normal C57BL/6 mice were seeded in a 24-well plate at a density of $1\times10^6$ cells/ml, treated with metformin (200 μM) or FK506 (100 nM) according to the experimental conditions, and then cultured for 3 days under anti-CD3 activation conditions (1 μg/ml). For the analysis using a flow cytometer, the cells were treated with an anti-CD4-percp antibody and an anti-CD25-APC antibody, reacted at 4° C. for 30 minutes, permeabilized, reacted with an anti-Foxp3-PE antibody, and then analyzed using the flow cytometer. To analyze the Treg activity, cells expressing a CD4+CD25+Foxp3 marker were gated and analyzed. For the results, the ratio of Foxp3+CD25+ cells to the whole cultured CD4+ T cells was plotted on a bar graph. The statistical analysis was carried out using a Graph prism (t-test, ANOVA), and the statistical significance was $p<0.05$.

As a result, it was revealed that the Treg activity increased when the cells were treated with metformin (FIG. 8B, Met) or FK506 (FK506) alone, compared to the control ((-)), whereas the Treg activity more remarkably increased when the cells were co-treated with metformin and FK506 (Met+FK506). That is, it can be seen that an effect of each drug on improvement of the Treg activity was further enhanced when the T cells were co-treated with metformin and FK506 in a cell experiment conducted under the T cell activation conditions.

<5-2> Metformin and Cyclosporine

Figure 9A:
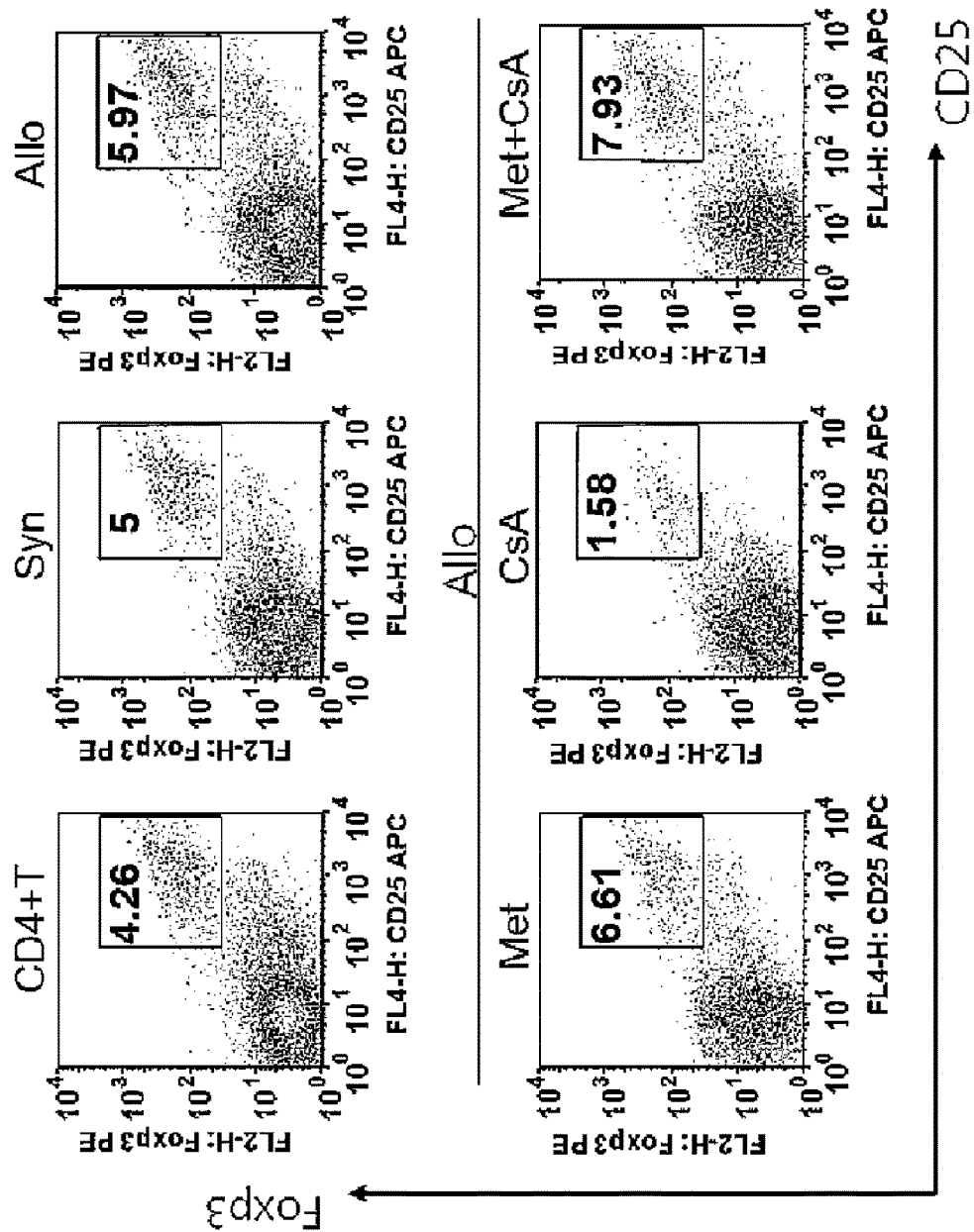
FIGS. 9A and 9B show experimental results of flow cytometry (FACS) showing an effect of metformin and CsA on activities of the Treg cells under the T cell activation conditions using the CD3 antibody.
Figure 9B:
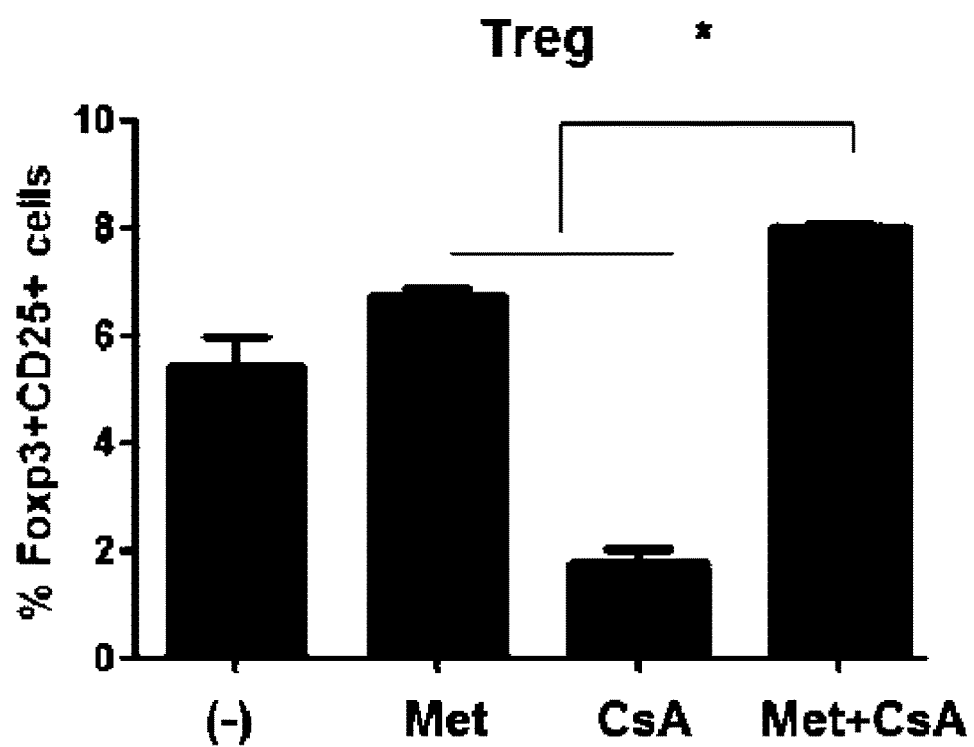

An effect of metformin and cyclosporine (CsA) on the activity of Treg cells was examined (FIGS. 9A and 9B). Splenocytes of mice were treated with metformin (1 mM) or CsA (100 nM) and cultured in the same manner as in Example <5-1>, and the ratio of Foxp3+CD25+ cells to the whole cultured CD4+ T cells was analyzed.

A level of Treg increased when the cells were treated with metformin (Met) alone, compared to the control (FIG. 9B, (-)), whereas the level of Treg remarkably decreased when the cells were treated with CsA (CsA) alone. On the other hand, it was revealed that the Treg activity more remarkably increased when the cells were co-treated with metformin and CsA (Met+CsA), compared to when the cells were treated with CsA alone and also treated with metformin alone. Therefore, it was confirmed that a combination of metformin and CsA had an effect of highly improving the Treg activity suppressed by CsA when the cells were treated with metformin and CsA.

EXAMPLE 6

Figure 10:
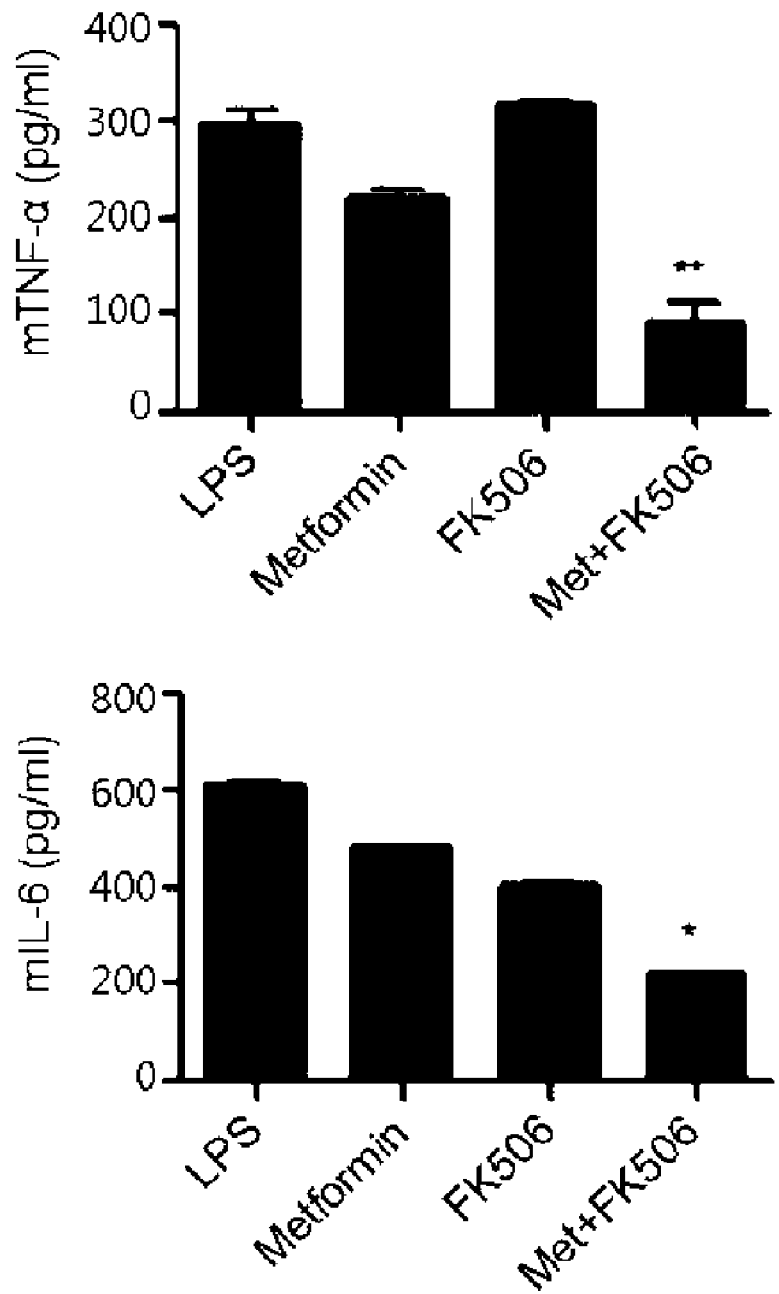
FIG. 10 shows ELISA experimental results showing an effect of metformin and FK506 on secretion rates of the inflammatory cytokines TNF-$\alpha$ and IL-6 secreted by splenocytes which have been cultured after treatment with lipopolysaccharides (LPS). * and ** represent statistical significances.
Figure 11:
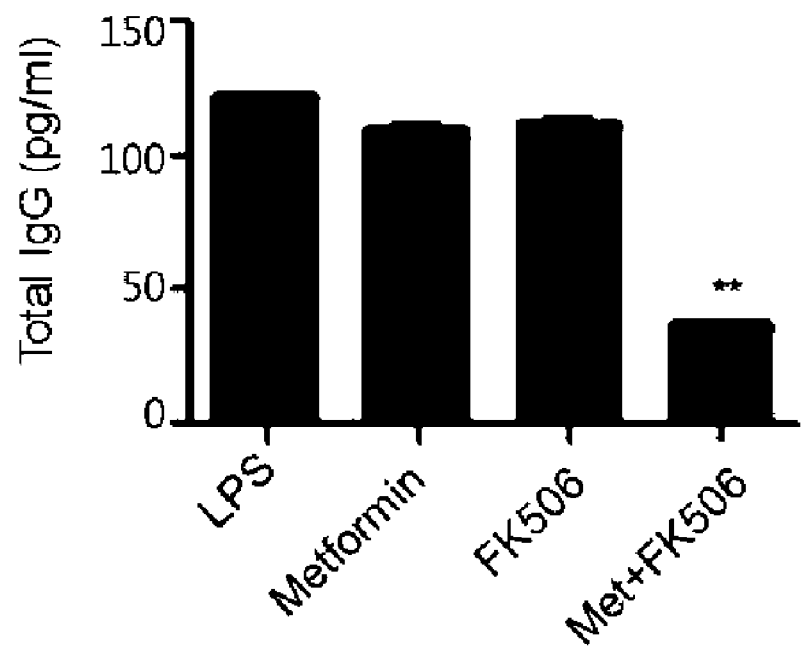
FIG. 11 shows ELISA experimental results showing an effect of metformin and FK506 on a level of immunoglobulins (IgG) secreted by the splenocytes which have been cultured after treatment with LPS. ** represents a statistical significance.

Effect of Co-Administration of Metformin on Levels of Inflammatory Cytokines and Immunoglobulins Secreted by Splenocytes To check an effect of metformin and a calcineurin inhibitor on the activity of inflammatory cytokines, effects of metformin and FK506 on levels of inflammatory cytokines (FIG. 10) and immunoglobulins (FIG. 11) secreted by splenocytes were compared. Splenocytes obtained from normal C57BL/6 mice were seeded in a 24-well plate at a density of $1 \times 10^6$ cells/ml, stimulated with LPS (100 ng/ml), treated with metformin (200 μM) or FK506 (100 nM) according to the experimental conditions, and then cultured for 3 days. Concentrations of TNF-α and IL-6 present in the resulting culture broth were measured to compare the drug effects (FIG. 10). Also, a concentration of immunoglobulins (IgG) present in the culture broth was measured in the same cell culture conditions to compare the drug effects (FIG. 11). The statistical analysis was carried out using a Graph prism (t-test, ANOVA), and the statistical significance was $p<0.05$.

As a result, when the cells were treated with metformin (FIG. 10, Metformin) or FK506 (FK506) alone, the concentrations of TNF-α and IL-6 in the culture broth were not highly reduced, compared to the control (LPS). On the other hand, when the cells were co-treated with metformin and FK506 (Met+FK506), the concentrations of both TNF-α and IL-6 tended to remarkably decrease to a statistically significant level, compared to the group in which the cells were treated with metformin or FK506 alone. This was similar to the effect of the co-treatment with metformin and FK506 on the secretion rate of the inflammatory cytokines of the T cells, as proven in <Example 3>. Therefore, it can be seen that an inhibitory effect on the secretion of the inflammatory cytokines was further enhanced even when the splenocytes stimulated with LPS were co-treated with metformin and FK506.

Likewise, in the case of the immunoglobulins, it was also revealed that the concentration of the immunoglobulins present in the culture broth was not significantly changed when the cells were treated with metformin (FIG. 11, Metformin) or FK506 (FK506) alone, compared to the control (LPS), whereas the concentration of the immunoglobulins was remarkably reduced when the cells were co-treated with metformin and FK506 (Met+FK506), compared to the group in which the cells were treated with metformin or FK506 alone.

EXAMPLE 7

Effect of Co-Administration of Metformin on Th17 and Treg Cell Groups of Liver Transplant Patient <7-1> Metformin and FK506

Figure 12:
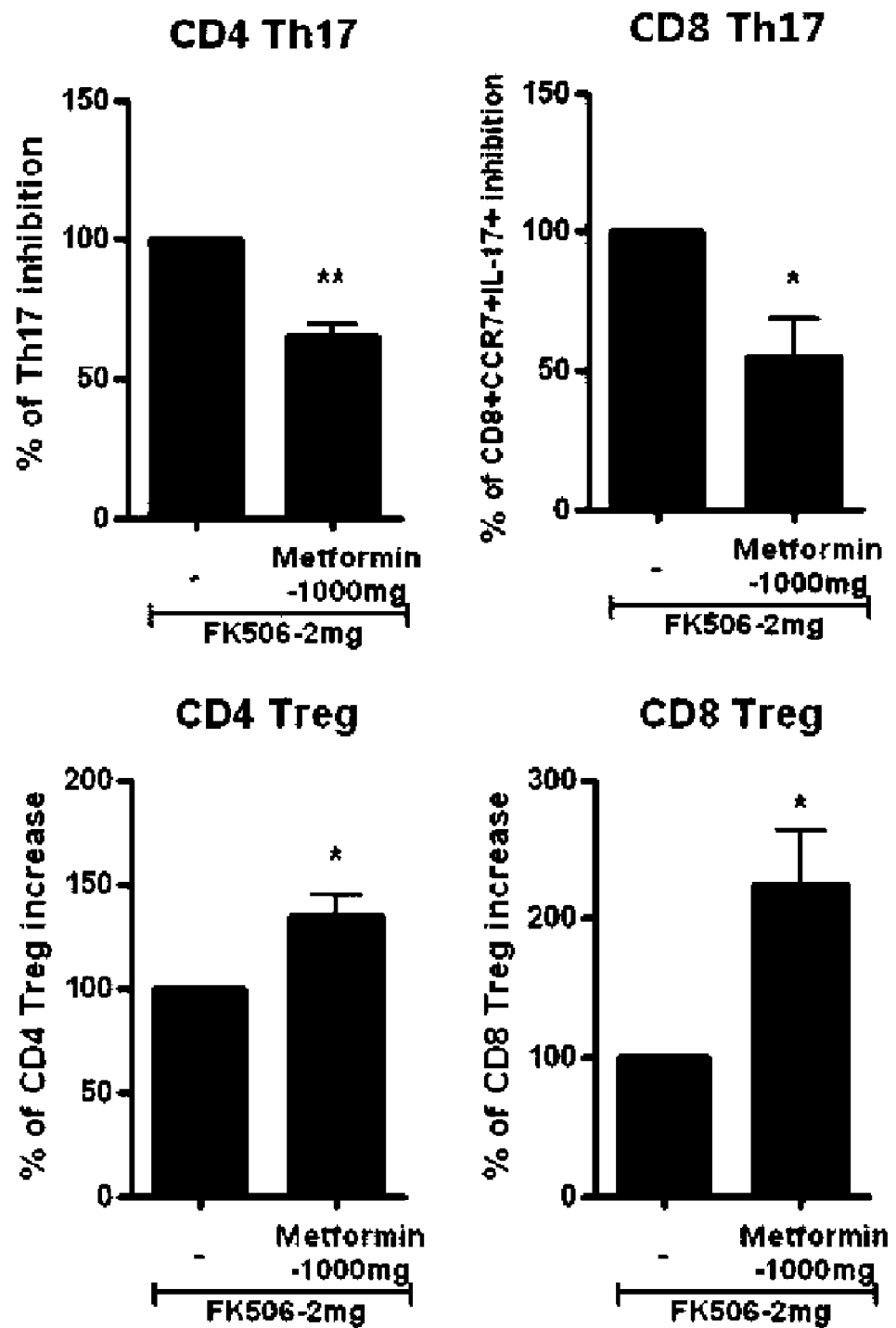
FIG. 12 shows experimental results of flow cytometry (FACS) showing an effect of co-administration of FK506 and metformin on T cell groups in a liver transplant patient. * and ** represent statistical significances.

An effect of co-administration of metformin and FK506 on T cell groups in patients receiving organ transplantation was examined (FIG. 12). Six patients who had taken FK506 (at a dose of 2 mg/day based on a patient weighing 60 kg) as an immunosuppressive drug after liver transplantation were allowed to take metformin (at a dose 1,000 mg/day based on a patient weighing 60 kg) for another 3 months. Thereafter, blood was collected from the patients before and after medication of metformin, and the ratios of the Treg and Th17 cell groups were measured. The liver transplant patients suffered from diabetes after a period of 5 to 10 years elapsed after the transplantation.

Specifically, peripheral blood mononuclear cells were isolated from the blood of each patient, treated with each of anti-CD4-percp, anti-CD8-APC, anti-CD25-APC, and anti-CCR7 Percp antibodies under the corresponding conditions, and then reacted at 4° C. for 30 minutes. Thereafter, the cells were permeabilized, reacted with each of anti-Foxp3-FITC and anti-IL-17-PE fluorescent antibodies, then analyzed using a flow cytometer and a FlowJo program. Based on the criteria for cell classification through the flow cytometry, CD4 Th17 cells were cells expressing both CD4 and IL-17, CD8 Th17 cells were cells expressing all CD8, CCR7, and IL-17, CD4 Treg cells were cells expressing CD4 and Foxp3 and having a high expression level of CD25, and CD8 Treg cells were cells expressing CD8 and Foxp3 and having a high expression level of CD25. The data were expressed by converting rates of decrease and increase of cells after medication of metformin when it was assumed that an expression level in Th17 or Treg cells before the medication was set to 100%, and the statistical significance was judged with a T-test using Prism software (* $p<0.05$, and ** $p<0.01$ in FIG. 12).

As a result, it can be seen that the CD4 Th17 and CD8 Th17 cell groups were remarkably reduced, but the CD4 Treg and CD8 Treg cell groups were remarkably increased after FK506 and metformin were co-administered for 3 months (FK506-2 mg/Metformin-1000 mg), compared to before the medication of metformin, that is, compared to the group in which FK506 was administered alone (FIG. 12, FK506-2 mg/−). Therefore, it can be seen that the co-administration of FK506 and metformin was effective in effectively suppressing Th17 which caused an immune rejection response in the liver transplant patients and increasing Treg which played a role in immunological tolerance dynamics, which was consistent with what was observed in the cell experiment.

<7-2> Metformin and Cyclosporine

Figure 13:
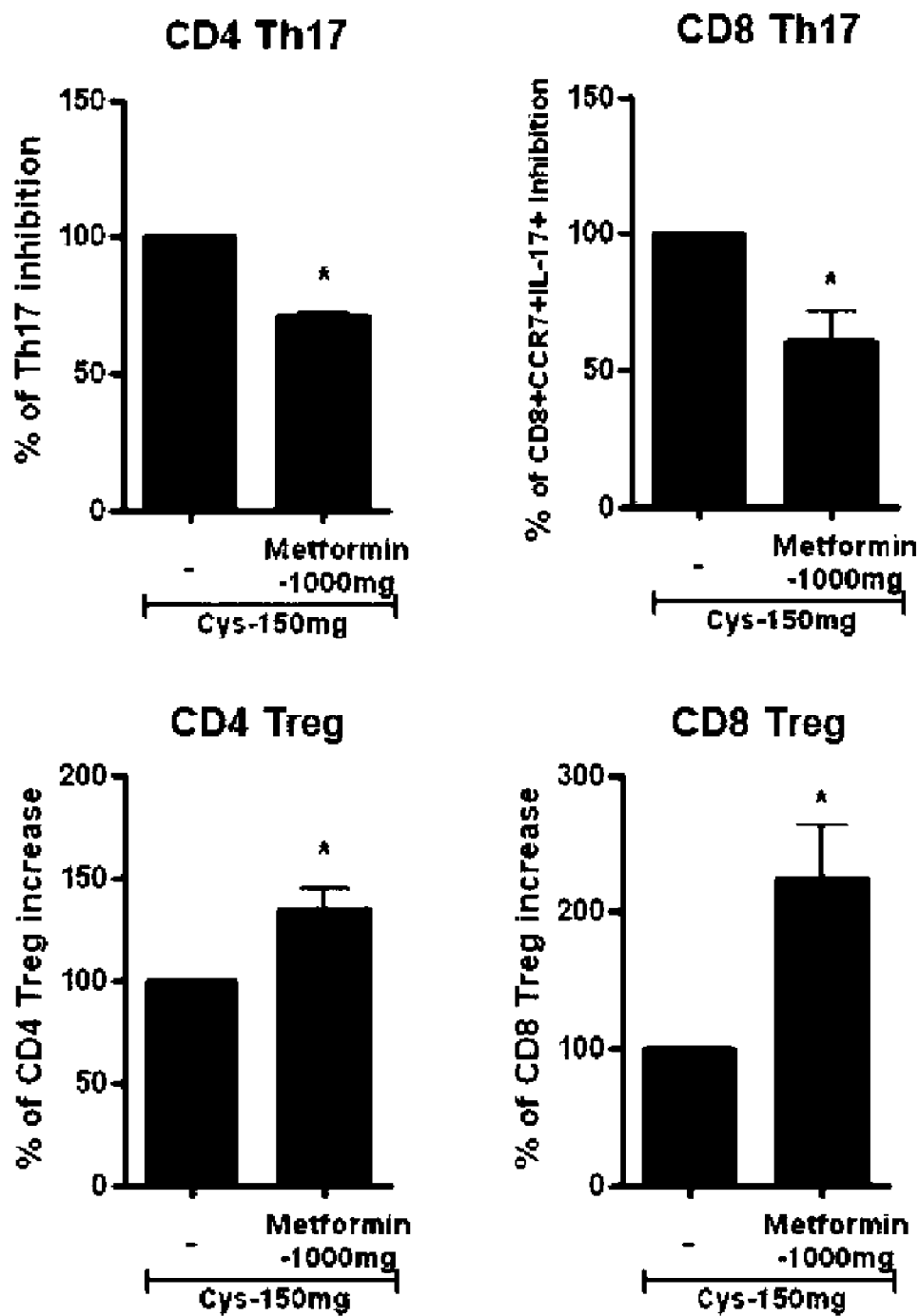
FIG. 13 shows experimental results of flow cytometry (FACS) showing an effect of co-administration of cyclosporine and metformin on the T cell groups in a liver transplant patient. * and ** represent statistical significances.

An effect of co-administration of metformin and cyclosporine (Cys) on T cell groups in patients receiving organ transplantation was examined (FIG. 13). Three patients who had taken cyclosporine (Cys at a dose of 150 mg/day based on a patient weighing 60 kg) as an immunosuppressive drug after liver transplantation were allowed to take metformin (at a dose 1,000 mg/day based on a patient weighing 60 kg) for another 3 months. Thereafter, blood was collected from the patients before and after medication of metformin, and the ratios of the Treg and Th17 cell groups were measured. The liver transplant patients suffered from diabetes after a period of 5 to 10 years elapsed after the transplantation. The experimental method and data analysis method were performed in the same manner as in Example <7-1>.

As a result, it can be seen that the Th17 cell group was reduced, but the Treg cell group was remarkably increased after cyclosporine and metformin were co-administered (Cys-150 mg/Metformin-1000 mg), compared to before the medication of metformin, that is, compared to the group in which cyclosporine was administered alone (FIG. 13, Cys-150 mg/−). Therefore, it can be seen that the co-administration of cyclosporine and metformin was more effective in effectively suppressing Th17 which caused an immune rejection response in liver transplant patients and increasing Treg which played a role in immunological tolerance dynamics, as observed upon the co-administration of FK506 and metformin in Example <7-1>.

Therefore, the present invention provides a composition for reducing nephrotoxicity caused by an immunosuppressive drug, which includes metformin as an active ingredient, and a pharmaceutical composition and a pharmaceutically combined preparation for preventing or treating an immune disease, which includes metformin and a calcineurin inhibitor as active ingredients. The composition according to the present invention can be useful in preventing or treating transplant rejection requiring the immunosuppression, an autoimmune disease, and inflammatory disease, etc. since the composition has effects of effectively alleviating a decline in renal function caused due to the side effect of conventional immunosuppressive drugs and further improving an immunosuppressive therapeutic effect.

INDUSTRIAL APPLICABILITY

As described above, the composition according to one exemplary embodiment of the present invention can be useful in effectively alleviating a decline in renal function caused due to the side effects of conventional immunosuppressive drugs, thereby enhancing a therapeutic effect to treat diseases in patient in need of immunosuppression. Also, the pharmaceutical composition or combined preparation according to another exemplary embodiment of the present invention is highly industrially applicable since the pharmaceutical composition or combined preparation is effective in preventing or treating organ transplant rejection, an autoimmune disease, an inflammatory disease, and the like by presenting various methods of co-administering a conventional immunosuppressive drug and metformin so as to reduce the nephrotoxic side effects of the conventional immunosuppressive drug and maximize an immunosuppressive or immunomodulatory effect.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A method of treating nephrotoxicity caused by an immunosuppressive drug, comprising:
   1) selecting a subject with nephrotoxicity caused by an immunosuppressive drug; and
   2) administering metformin or a pharmaceutically acceptable salt thereof to the subject.

2. The method of claim 1, wherein the immunosuppressive drug is a calcineurin inhibitor.

3. The method of claim 2, wherein the calcineurin inhibitor comprises cyclosporine or tacrolimus.

4. A method of treating an immune disease, comprising: administering a calcineurin inhibitor and metformin or a pharmaceutically acceptable salt thereof to a subject with an immune disease.

5. The method of claim 4, wherein the calcineurin inhibitor comprises cyclosporine or tacrolimus.

6. The method of claim 4, wherein the calcineurin inhibitor and the metformin or pharmaceutically acceptable salt thereof are administered at a weight ratio of 1:1 to 1:3,500.

7. The method of claim 6, wherein the calcineurin inhibitor and the metformin or pharmaceutically acceptable salt thereof are administered at a weight ratio of 1:5 to 1:500.

8. The method of claim 5, wherein the cyclosporine is administered in an amount of 1 to 5 mg/day/kg of body weight.

9. The method of claim 5, wherein the tacrolimus is administered in an amount of 0.01 to 0.1 mg/day/kg of body weight.

10. The method of claim 4, wherein the metformin or pharmaceutically acceptable salt thereof is administered in an amount of 5 to 35 mg/day/kg of body weight.

11. The method of claim 4, wherein the immune disease is selected from the group consisting of acute or chronic organ transplant rejection, autoimmune diseases, and inflammatory diseases.

* * * * *